United States Patent [19]

Sato

[11] Patent Number: 5,282,471
[45] Date of Patent: Feb. 1, 1994

[54] ULTRASONIC IMAGING SYSTEM CAPABLE OF DISPLAYING 3-DIMENSIONAL ANGIOGRAM IN REAL TIME MODE

[75] Inventor: Takeshi Sato, Tochigiken, Japan

[73] Assignee: Kabushiki Kaisha Toshiba, Kawasaki, Japan

[21] Appl. No.: 919,954

[22] Filed: Jul. 27, 1992

[30] Foreign Application Priority Data

Jul. 31, 1991 [JP] Japan .................. 3-192195

[51] Int. Cl.⁵ .................................. A61B 8/06
[52] U.S. Cl. .................. 128/660.07; 128/661.09; 128/916; 128/660.05
[58] Field of Search .......... 128/660.05, 660.07, 128/661.09, 661.08, 916

[56] References Cited

U.S. PATENT DOCUMENTS

| | | | |
|---|---|---|---|
| 4,747,411 | 5/1988 | Ledley | 128/916 |
| 5,072,734 | 12/1991 | Takeuchi | 128/661.09 |
| 5,090,411 | 2/1992 | Higuchi | 128/660.05 |
| 5,188,113 | 2/1993 | Sato et al. | 128/661.09 |

FOREIGN PATENT DOCUMENTS

2-36851 2/1990 Japan.

OTHER PUBLICATIONS

Duplex Scanner II: For Simultaneous Imaging of Artery Tissues and Flow, by Barber et al., Ultrasonics Symposium Proceedings, IEEE 1974, pp. 744–748.

*Primary Examiner*—William E. Kamm
*Assistant Examiner*—George Manuel
*Attorney, Agent, or Firm*—Oblon, Spivak, McClelland, Maier & Neustadt

[57] ABSTRACT

In an ultrasonic imaging system, an ultrasonic angiographic image of a blood vessel, equivalent to an X-ray angiographic image, is produced in a real time by utilizing an IIR digital filter with a ROM and a frame memory. The ultrasonic imaging system comprises: a scanning unit for scanning a biological body under medical examination within a three-dimensional scanning plane involving the biological body by utilizing ultrasonic pulses to obtain echo signals produced from echo pulses reflected from the biological body; an ultrasonic image data producing unit for producing a plurality of ultrasonic scanned image data about the scanned biological body with regard to the respective scanning planes in response to the echo signals; a bloodflow-distribution image data producing unit for producing a plurality of bloodflow-distribution image data about the scanned biological body with regard to the respective scanning planes in response to the echo signals; a storage unit for temporarily storing the plurality of bloodflow-distribution image data, while sequentially updating and superimposing the plural bloodflow-distribution image data with each other during a predetermined scanning period.

25 Claims, 23 Drawing Sheets

COLOR MONITOR 300

REAL-TIME 3-D ANGIOGRAM 400

REAL-TIME COLOR DOPPLER IMAGE 450

IIR DIGITAL FILTER 1000

BLOOD-FLOW DATA "$C_n$"

ROM 100

FRAME MEMORY 200

$V_{n-1}, W_{n-1}$

FLUOROSCOPIC IMAGE DATA "$V_n$"

DEPTH DATA "$W_n$"

B-MODE DATA

FLUOROSCOPIC
IMAGE DATA

ANGIOGRAPHIC
IMAGE DATA

COMBINED B-MODE DATA/
FLUOROSCOPIC IMAGE DATA

COMBINED B-MODE
DATA/ANGIOGRAM

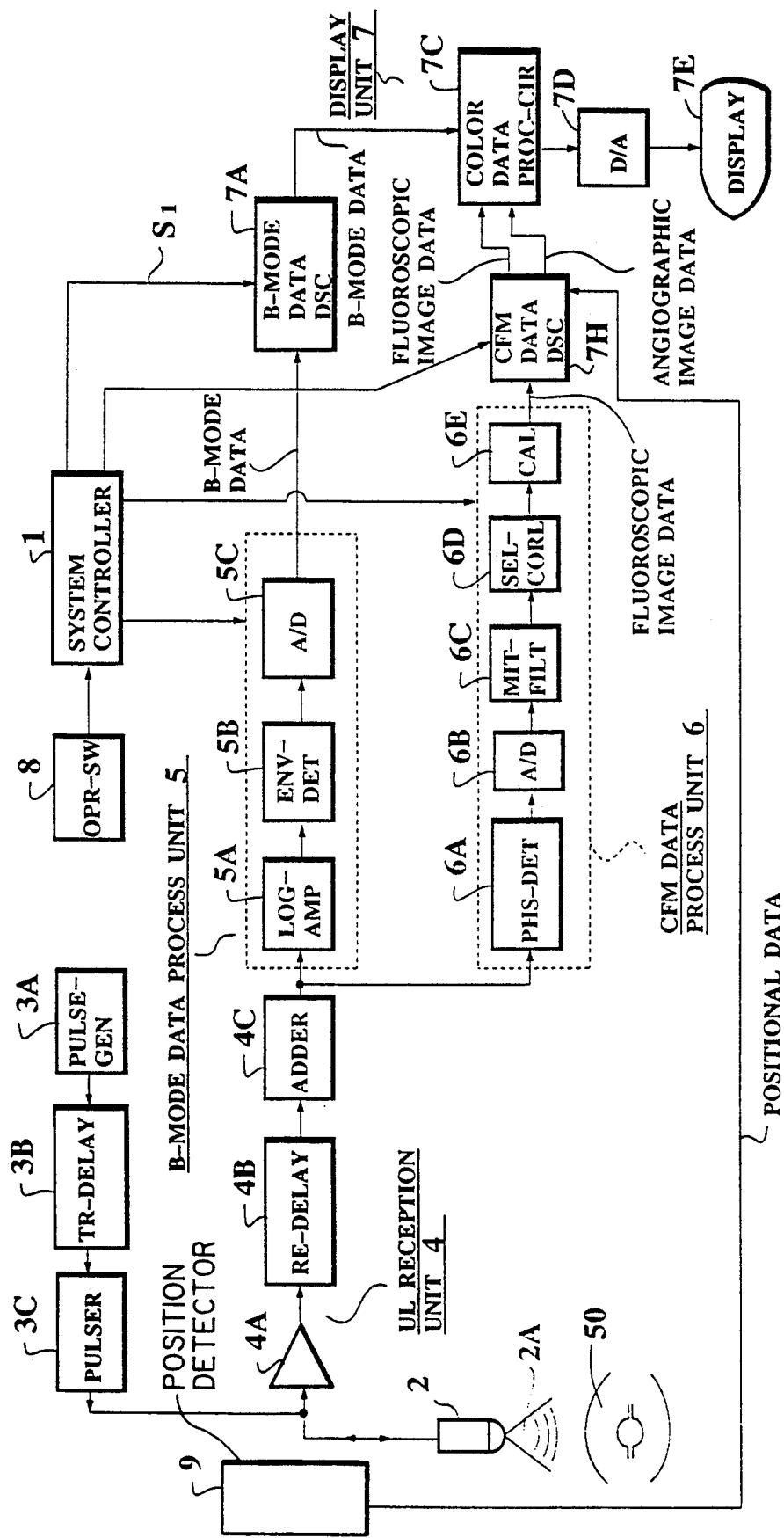

BLOOD VESSEL

SCANNING PLANE "A"
SCANNING PLANE "B"
SCANNING PLANE "C"

BLOOD VESSEL'S IMAGE IN SCANNING PLANE "B"

POSITIONAL SHIFT

BLOOD VESSEL'S IMAGE IN SCANNING PLANE "A"

ULTRASONIC IMAGING SYSTEM CAPABLE OF DISPLAYING 3-DIMENSIONAL ANGIOGRAM IN REAL TIME MODE

BACKGROUND OF THE INVENTION

1. Field of the Invention

The present invention generally relates to an ultrasonic imaging system. More specifically, the present invention is directed to an ultrasonic imaging system capable of displaying an angiogram of a biological body under medical examination in a real time mode, in combination with an ultrasonic image, e.g., a B-mode image of this biological body.

2. Description of the Prior Art

Various types of ultrasonic imaging systems or apparatuses have been proposed and/or marketed in the medical field. For instance, one conventional ultrasonic imaging apparatus has been proposed utilizing both the ultrasonic Doppler method and the pulse reflection method. In this ultrasonic imaging apparatus, each of a blood-flow distribution image and an ultrasonic image (for instance, a so-called "B-mode" image) of a biological body under medical examination are acquired by a single ultrasonic probe, and a color blood-flow distribution image is superimposed on a monochrome B-mode image, so that color blood-flow information is displayed in a real time mode together with such a superimposed image. This conventional apparatus is normally referred to an "ultrasonic blood-flow imaging apparatus". It should be noted that since the ultrasonic beam transmitted from the ultrasonic probe is scanned over only one plane within the biological body, the blood-flow distribution image and B-mode image indicate images of only this scanned plane. As a consequence, if a blood vessel is bent in a three-dimensional plane, the ultrasonic image as to only the scanned plane is displayed on the display monitor, so that blood-vessel images other than the above scanned blood-vessel image are not displayed at all. Even if either the scanning direction of the ultrasonic probe may be varied, or the scanning position thereof may be moved, only a portion of the blood flows for each scanning operation can be still monitored. Accordingly, it is very difficult to grasp conditions of the overall blood flow.

Conventionally, the X-ray fluoroscopic imaging apparatuses, instead of the above-described ultrasonic imaging apparatus, have been employed to investigate such an overall blood-flow condition, in which angiographic imaging operation is carried out for a biological body and then images of blood vessels (angiogram) containing 3-dimensional data are displayed.

However, there are many problems with employing such X-ray fluoroscopic imaging apparatuses instead of the ultrasonic imaging apparatuses so as to display angiograms of blood vessels. That is, firstly, the entire constructive arrangement of the X-ray imaging apparatus becomes complex and bulky, as compared with that of the ultrasonic imaging apparatus. Secondly, since X-ray beams are utilized to image the blood vessels, various restrictions are necessarily required in the X-ray imaging operation and also medical care. As a consequence, such an ultrasonic imaging system capable of performing blood-vessel imaging equivalent to X-ray fluoroscopic imaging has been strongly desired in the medical field.

To achieve such a strong demand, the Applicants have proposed in Japanese KOKAI (Disclosure) patent application No. 2-36851 (opened on Feb. 6, 1990), and Japanese patent application No. 2-401139 (filed on Dec. 10, 1990), the ultrasonic imaging apparatuses capable of displaying a 3-dimensional blood vessel image. In these ultrasonic imaging apparatuses, a plurality of ultrasonic image (bloodflow distribution image) data are stored in a plurality of frame memories, these ultrasonic image data are weighted with proper weighting values in accordance with the acquired position of the B-mode image during the data reading operation, and then all of these bloodflow distribution image data are added with each other, so that brightness of the bloodflow distribution image data is varied in accordance with the acquired positions of the image data in order to represent or express a perspective view.

Nevertheless, these conventional ultrasonic imaging apparatuses capable of displaying such a quasi-X-ray three-dimensional angiogram are not yet satisfactory in terms of a real-time display and a simple construction, which are strongly required by many operators in the medical field. Precisely speaking, since the 3-dimensional angiogram is produced by first storing the plural bloodflow distribution image data into the plural frame memories, and secondly reading these image data, and finally adding them with each other, a large memory capacity of these frame memories is required, and therefore a large-scaled circuit arrangement is needed. Moreover, there is no suggestion of a real-time display of 3-dimensional angiogram in these conventional ultrasonic imaging apparatus capable of displaying the 3-dimensional angiogram.

SUMMARY OF THE INVENTION

The present invention has been made in an attempt to solve the above described problems, and therefore, has an object to provide an ultrasonic imaging system capable of displaying an angiogram of a biological body in a real time mode, which is essentially equivalent to an X-ray fluoroscopic image, by utilizing ultrasonic pulses.

Another object of the present invention is to provide an ultrasonic imaging system capable of displaying a real-time three-dimensional angiogram with a simple circuit arrangement and an easy operability.

To achieve the above-described objects, an ultrasonic imaging system according to the present invention, comprises:

scanning means (2, 3, 4) for scanning a biological body (50) under medical examination within a three-dimensional scanning plane involving the biological body (50) by utilizing ultrasonic pulses (2A) to obtain echo signals produced from echo pulses reflected from the biological body (50);

ultrasonic image data producing means (5) for producing a plurality of ultrasonic scanned image data about the scanned biological body (50) with regard to the respective scanning planes in response to said echo signals;

bloodflow-distribution image data producing means (6) for producing a plurality of bloodflow-distribution image data about the scanned biological body (50) with regard to the respective scanning planes in response to said echo signals;

storage means (14:15:1000:140:148) for temporarily storing said plurality of bloodflow-distribution image data, while sequentially updating and superimposing said plural bloodflow-distribution image data with each other during a predetermined scanning period; and display means (7) for displaying a bloodflow-distribution image superimposed on an ultrasonic scanned image by processing both of said bloodflow-distribution image data acquired during said predetermined scanning period and said ultrasonic scanned image data.

Furthermore, according to the present invention, an ultrasonic imaging system comprises:

scanning means (2, 3, 4) for scanning a biological body (50) under medical examination within a three-dimensional scanning plane involving the biological body (50) by utilizing ultrasonic pulses (2A) to obtain echo signals produced from echo pulses reflected from the biological body (50);

ultrasonic image data producing means (5) for producing a plurality of ultrasonic scanned image data about the scanned biological body (50) with regard to the respective scanning planes in response to said echo signals;

bloodflow-distribution image data producing means (6) for producing a plurality of bloodflow-distribution image data about the scanned biological body (50) with regard to the respective scanning planes in response to said echo signals;

storage means (14:15:1000:140:148) for temporarily storing said plurality of bloodflow-distribution image data, while sequentially updating and superimposing said plurality of bloodflow-distribution image data in such a manner that preceding bloodflow-distribution image data is updated/superimposed with present bloodflow-distribution image data; and display means (7) for displaying a bloodflow-distribution image superimposed on an ultrasonic scanned image in a real time mode by processing both of latest bloodflow-distribution image data acquired during a predetermined scanning period and said ultrasonic scanned image data.

BRIEF DESCRIPTION OF THE DRAWINGS

For a better understanding of the present invention, reference is made of the following detailed description in conjunction with the accompanying drawings, in which:

FIG. 16 is a schematic block diagram of a sixth ultrasonic imaging system according to the present invention;

DETAILED DESCRIPTION OF THE PREFERRED EMBODIMENTS

Before describing various preferred embodiments of an ultrasonic imaging system according to the present invention, the basic concept of the present invention will now be summarized.

In the ultrasonic imaging system accomplished by the basic idea of the present invention, for instance, a 3 D (dimensional) angiogram 400 of a biological body (not shown) is displayed in a real time mode on a left-half color monitor 300A and simultaneously a color Doppler image 450 thereof is displayed in a real time mode on a right-half color monitor 300B. Accordingly, since any operators can observe the real-time color Doppler image 450 while investigating the real-time 3-D angiogram 400, optimum 3-dimensional scanning operations can be achieved by feeding back the investigated information of the real-time 3-D (dimensional) angiogram 400 to the probe scanning manipulation. That is, operators can readily find out the best way to obtain the 3-D angiograms under optimum conditions, because they can check it while observing such real-time angiograms on the color monitor 300 in conjunction with the real-time color Doppler image 450 displayed on the same color monitor 300.

Figure 2:
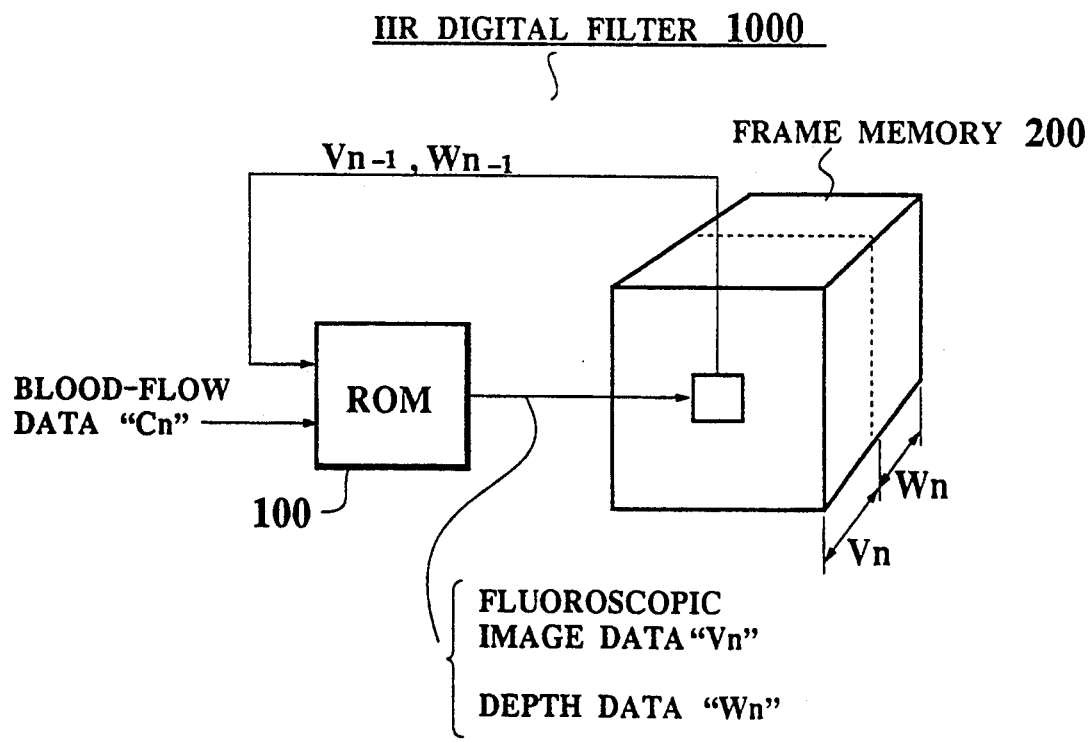
FIG. 2 schematically illustrates an IIR digital filter 1000 for realizing the basic idea of the present invention.

To achieve the real-time display of the angiogram 400, it is preferable to employ an IIR (Infinite Impulse Response) digital filter 1000 as shown in FIG. 2. This IIR digital filter 1000 is mainly constructed of a ROM (Read-Only Memory) 100 and a single frame memory 200.

With employment of the IIR digital filter 1000 shown in FIG. 2, the above-described basic idea of the present invention may be realized by forming a 3-dimensional angiogram, while executing the following algorithm. In this algorithm, symbol "$C_n$" indicates data about a present bloodflow velocity; symbol "$V_n$" shows present fluoroscopic image data; symbol "$V_{n-1}$" denotes fluoroscopic image data acquired during 1 preceding frame; symbol "$W_n$" represents present depth data; symbol "$W_{n-1}$" is depth data acquired during 1 preceding frame; and symbol "$C_{th}$" shows a parameter used to judge whether or not an actual bloodflow is obtained based upon the bloodflow velocity. It should be noted that an initial value is given as follows: $V_o = W_o = 0$.

```
if abs(Cn) < Cth
    then
        Vn = Vn-1
        Wn = Wn-1 + 1
        if Wn > 63
            then
                Vn = 0
                Wn = 0
        endif
    else
        Vn = Cn
        Wn = 1
    endif
```

First, upon receipt of the present bloodflow data "$C_n$" for each frame, the ROM 100 judges whether or not there exists bloodflow data in the frame.

A case of $abs(C_n) < V_{th}$ corresponds to such a case where no bloodflow data is present. Under such a circumstance, the past, or preceding image data is written into the single frame memory 200 and the depth data is increased by 1.

To the contrary, if there is bloodflow data, namely, $abs(C_n) \geq C_{th}$, the latest image data is written into the frame memory 200 and the depth data is set to 1.

Figure 1:
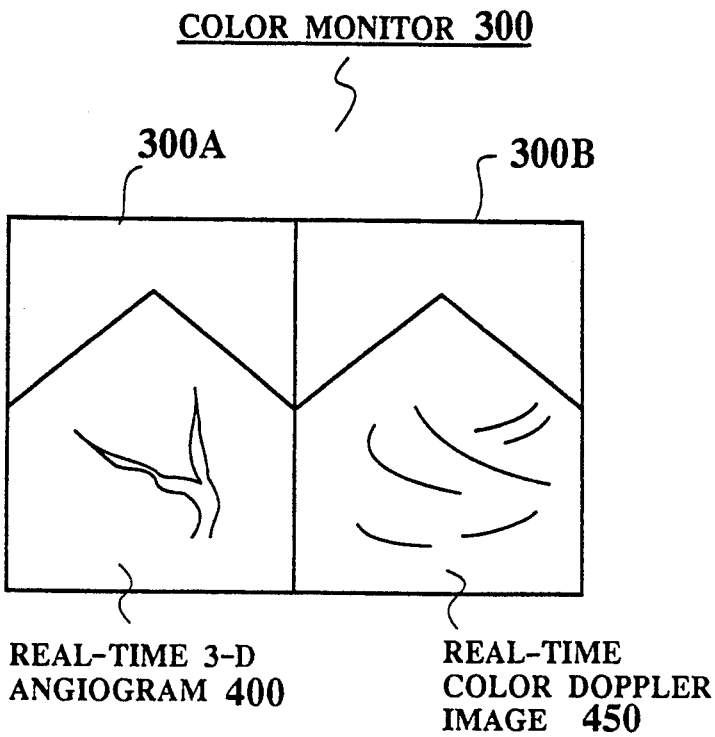
FIG. 1 represents both a real-time 3-D angiogram 400 and a real-time color Doppler image 450 for explaining a basic idea of the present invention.

Since the above-described operation is cyclically executed for each pixel of the ultrasonic image, the above-described 3-dimensional angiogram is formed while the image data are written into this single frame memory. As a result, since these image data are read out from the frame memory 200 and then supplied to the monitor 300 of FIG. 1, the real-time 3-dimensional angiogram 400 produced by the ultrasonic pulses is displayed on the left-half monitor 300A in combination with the color Doppler image 450 in a real time mode. In other words, such a real-time 3-D angiogram may be displayed with only one frame memory 200 having a small memory capacity.

OVERALL ARRANGEMENT/OPERATION OF FIRST ULTRASONIC IMAGING SYSTEM

Figure 3:
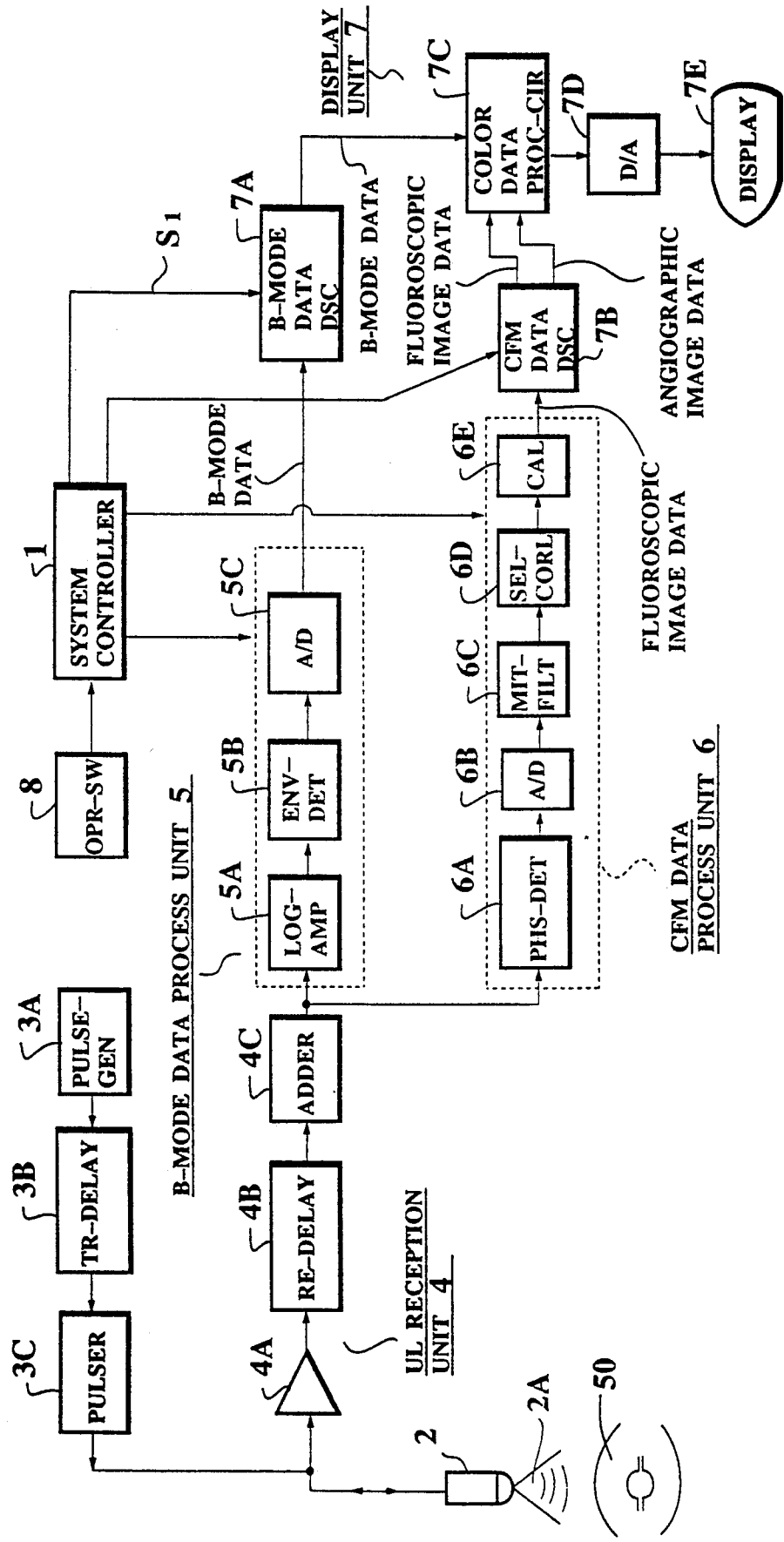
FIG. 3 is a schematic block diagram of an overall arrangement of an ultrasonic imaging system according to a first preferred embodiment of the present invention.

Referring now to FIG. 3, an overall arrangement of an ultrasonic imaging system capable of displaying a real-time 3-dimensional angiogram, according to a first preferred embodiment of the present invention, will be described.

The first ultrasonic imaging system represented in FIG. 3 is mainly constructed of a system controller 1, an ultrasonic probe 2, an ultrasonic pulse transmission unit 3, an ultrasonic pulse reception unit 4, a B-mode data process unit 5, a CFM (color flow mapping) data process unit 6, a display unit 7 and an operation switch 8.

The ultrasonic probe 2 is of a sector scanning type. The sector scanning type ultrasonic probe 2 is constituted by a large number of transducer elements (not shown in detail) aligned along one line. An ultrasonic beam 2A is electronically scanned in a fan shape and is electronically focused onto a biological body 50 under medical examination by changing the voltage applications timings to the respective transducer elements. Furthermore, this ultrasonic probe 2 is controlled in such a manner that an ultrasonic scanning plane by the beam 2A can be changed within a three-dimensional space.

The ultrasonic pulse transmission unit 3 includes a pulse generator 3A, a transmission pulse delay circuit 3B and a pulser 3C. In this ultrasonic pulse transmission unit 3, a rate pulse is generated by the pulse generator 3A and then delayed in the transmission pulse delay circuit 3B. That is, this pulse delay circuit 3B gives predetermined delay times to the rate pulses for the corresponding transducer elements in order to focus the ultrasonic beam 2A to a predetermined direction, so that delayed rate pulse are supplied to the pulser 3c. In response to the delayed rate pulses received from the transmission pulse delay circuit 3B, the respective transducer elements of the ultrasonic probe 2 are repeatedly driven for a predetermined driving time by this pulser 3c.

When the ultrasonic probe 2 is driven by the ultrasonic pulse transmission unit 3, the ultrasonic pulse beam 2A is transmitted from this probe 2 to the biological body 50, and then received by Doppler shifts from blood flows within the biological body 50. Then, the ultrasonic echoes are reflected from the biological body 50 and thereafter received by the same transducer elements of the ultrasonic probe 2 to be derived as ultrasonic echo signals.

On the other hand, the ultrasonic pulse reception unit 4 includes a preamplifier 4A, a reception pulse delay circuit 4B, and an adder 4C. In this reception unit 4, the above-described ultrasonic echo signals derived from the ultrasonic probe 2 are amplified to a predetermined signal level in the preamplifier 4A. Then, the amplified echo signals are supplied to the reception signal delay circuit 4B. The reception signal delay circuit 4B gives preselected delay times to the echo signals amplified in the preamplifier 4A with respect to each of the transducer elements in such a manner that the delay times given to the rate pulses in the transmission signal delay circuit 3B are returned to original times. The echo signals which have been delayed in the reception signal delay circuit 4B, are added with each other in the adder 4C, and then the added echo signal is supplied to the B-mode data process unit 5 and the CFM data process unit 6.

The B-mode data process circuit 5 is constituted by a logarithm amplifier 5A, an envelope detecting circuit 5B and an A/D converter 5C, and performs the following data process under control of the system controller 1. In the B-mode data process unit 5, the added echo signal from the adder 4C is logarithmic-amplified in the logarithm amplifier 5A and the logarithmic-amplified echo signal is envelope detected in the envelope detecting circuit 5B. The envelope-detected echo signal is A/D-converted by the A/D converter 5C into the B-mode image data (ultrasonic echo image). Thereafter, the B-mode image data is supplied to the display unit 7.

On the other hand, the CFM data process system 6 is arranged by a phase detecting circuit 6A, an A/D converter 6B, an MTI filter 6C, a self-correlator 6D, and a calculator unit 6E, which are operated under the control of the system controller 1. In this CFM data process unit 6, the added echo signal from the adder 4C is phase-detected in the phase detecting circuit 6A, namely quadrature-detected therein, and a high frequency signal component of the phase-detected echo signal is removed by a low-pass filter (not shown in detail), so that a Doppler shifted signal, or a Doppler-detected output used for a bloodflow image is obtained from the phase detecting circuit 6A. Generally speaking, this Doppler-detected output contains an unnecessary reflection signal such as a clutter signal component reflected from a slow moving article e.g., a cardiac wall other than the bloodflow information. Accordingly, this Doppler detected signal is processed in the A/D converter 6B, and the MTI (Moving Target Indicator) filter 6C. This moving target indicator filter 6C is well known in the radar field, and functions to detect only a moving target by way of the Doppler effect. Therefore, the MTI filter 6C can detect movements of bloodflows based upon the phase changes among the same pixels in the rate pulses which have been repeatedly transmitted for a predetermined time, and also can remove the clutter signal component from the Doppler detected signal.

To analyze the frequencies of the Doppler detected data having no clutter signal component, the self-correlator 6D is employed in the preferred embodiment. This self-correlator 6D functions to perform a two-dimensional multi-point analysis in a real time mode. The calculation steps of this 2-D multipoint analysis are less than those of the FFT (Fast Fourier Transformation) method.

The calculating unit 6F is composed of an average velocity calculation unit, a dispersion calculation unit, and a power calculation unit, although not shown in FIG. 3. In this calculation unit 6E, an average Doppler-shift frequency "fd" is calculated from the frequency analyzed Doppler-detected data of the self-correlator 6D in the average-velocity calculation unit, dispersion "$\delta^2$" is obtained in the dispersion calculation unit, and then total power "TP" is calculated in the power calculation unit.

It should be noted that the total power is directly proportional to the strength of scattered echoes derived from the bloodflow, from which echoes reflected from the moving article having a frequency lower than the cut-off frequency of the MTI filter 6C have been removed. As described above, the bloodflow data obtained from the CFM data process unit 6 is supplied to the display unit 7.

The display unit 7 includes a B-mode data DSC (Digital Scan Converter) 7A, a CFM data DSC 7B, a color data process circuit 7C, a D/A converter 7D, and a color monitor 7E.

INTERNAL ARRANGEMENT OF CFM DATA DSC 7B

Figure 4:
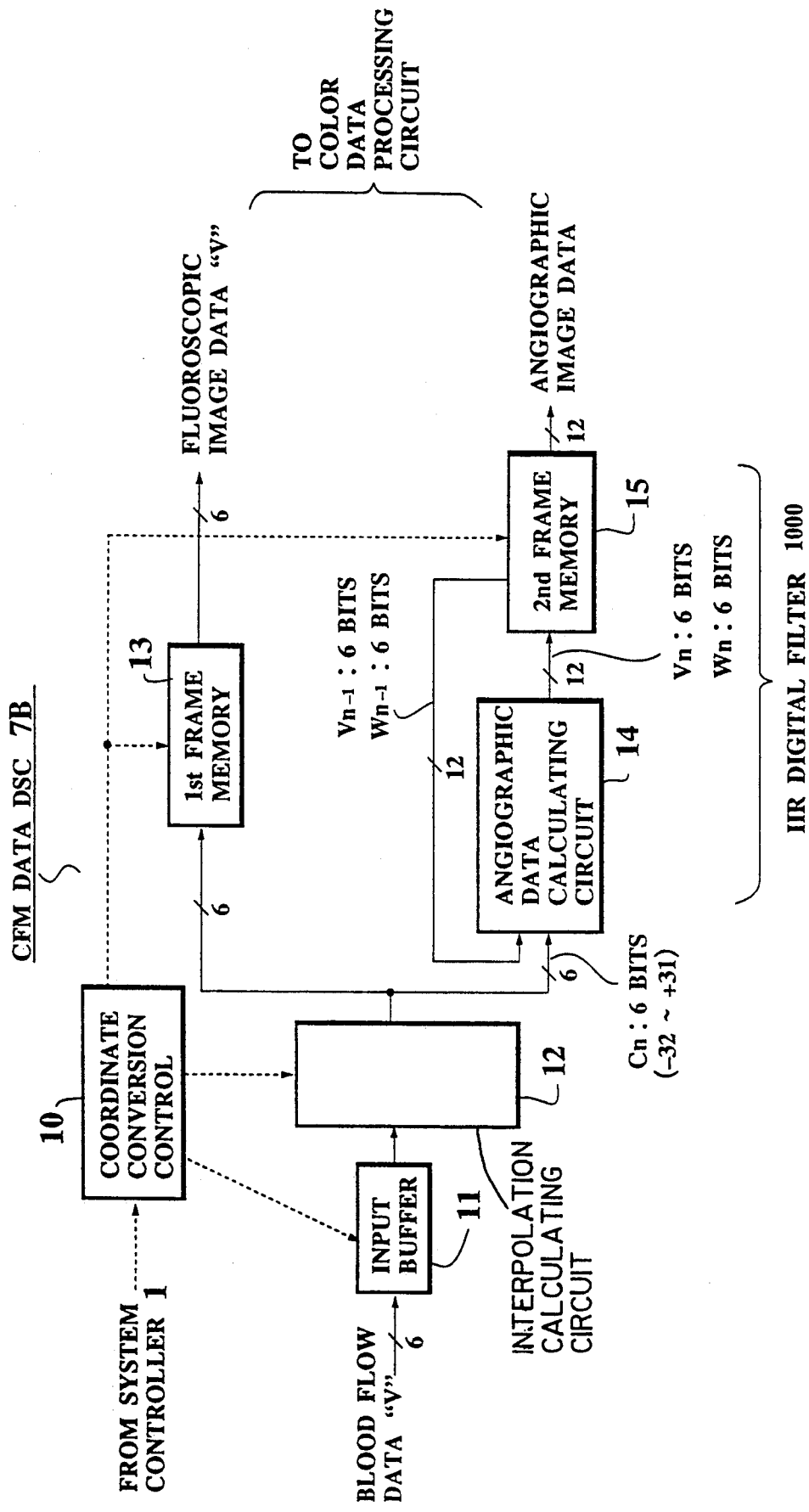
FIG. 4 is an internal circuit diagram of the CFM DSC 7B shown in FIG. 3.

As shown in FIG. 4, the CFM data DSC 7B employed in the display unit 7 of FIG. 3 is arranged by a coordinate conversion control circuit 10, a plurality of input buffers 11, an interpolation calculating circuit 12, a first frame memory 13, an angiographic data calculating circuit 14 and a second frame memory 15. In FIG. 4, a solid line indicates a data flow, whereas a dot line denotes a control signal flow. In the CFM data DSC 7B, the velocity (bloodflow) data having, for instance, 6 bits supplied from the CFM data process unit 6 of FIG. 3 are switched for the respective resters and then inputted into a plurality of input buffers 11. The coordinate conversion control circuit 10 converts a polar coordinate system into a rectangular coordinate system, and also furnishes an address for reading the data from these input buffers 11, an interpolation coefficient, and an address for writing the data into the first and second frame buffers 13 and 15. Under such a control of the coordinate conversion control circuit 10, the data read out from the respective input buffer 11 are interpolated in the interpolation calculating circuit 12, and the interpolated data are written into the first from data 13. At the same time, the interpolated data are supplied to the angiographic data calculating circuit 14.

This angiographic data calculating circuit 14 corresponds to the above-described ROM 100 of the IIR digital filter 1000 shown in FIG. 2. That is, both the angiographic data calculating circuit 14 and the second frame memory 15 may be realized by employing the IIR digital filter 1000 of FIG. 2. As previously stated, the angiographic data calculating circuit 14 and the second frame memory 15 constitute the featured circuit arrangement of the present invention, an operation of which will now be described more in detail.

Assuming now in this first preferred embodiment that interpolated data is indicated by "$C_n$" (6 bits, −32 to +31), data to be written into the second frame memory 15 by the calculation are shown by "$V_n$" (6 bits, −32 to +31) and "$W_n$" (6 bits, 0 to +63), and also data of the second frame memory 15 before being written therein, which have been read out from the same addresses as the write addresses, are denoted by "$V_{n-1}$" (6 bits, −32 to +31) and "$W_{n-1}$" (6 bits, 0 to +63), upon receipt of the interpolated data "$C_n$" for 1 frame, the angiographic data calculating circuit 14 judges whether or not there exists bloodflow data in this 1 frame. This judgement is performed by comparing "abs (absolute value) ($C_n$)" with the parameter "$C_{th}$". This parameter "$C_{th}$" is a parameter having 4 for removing the noise.

It should be noted that the above-described symbols (+, −) indicate that an incoming bloodflow is positive (+), whereas an outgoing bloodflow is negative (−), and also numeral values from 0 to 31 denote velocities of bloodflows. A high velocity bloodflow has a large numeral value.

In the angiographic data calculating circuit 14, the following process is carried out and the past, or preceding image data are written into the second frame memory 15 in the case of no bloodflow data, namely abs($C_n$)<$C_{th}$:

$$V_n = V_{n-1}$$
$$W_n = W_{n-1} + 1$$
of $W_n > 63$
then
$$V_n = 0$$
$$W_n = 0$$
endif This process is executed for echo of the pixels.

To the contrary, if there is bloodflow data, namely abs($C_n$)≧$C_{th}$, the following process is carried out, and the latest data are written into the second frame memory 15:

$$V_n = C_n$$

$$W_n = 1.$$

This process is similarly executed for each of the pixels.

Such a process operation may be realized by employing a ROM having a memory capacity of 256 Kbytes×16 bits.

As previously explained, it should be understood that when the data "$V_n$" and "$W_n$" are written into the second frame memory 15 by the angiographic data calculating circuit 14, this writing operation must be performed only once during a single ultrasonic beam scanning operation with regard to a certain address. In other words, the second frame memory 15 functions as a delay element for one frame.

Subsequently, both the fluoroscopic image data "V" which has been read from the first frame memory 13 in accordance with the television scanning direction of the color display 7E, and the angiographic data which has been read from the second frame memory 15 in accordance with the television scanning direction, are supplied to the color data process circuit 7C in combination with the B-mode image data which has been similarly read from the B-mode data DSC 7A in accordance with the television scanning direction for color image data processing purposes.

MODIFICATION OF ANGIOGRAPHIC DATA CALCULATING CIRCUIT

As previously described, the angiographic data calculating circuit 14 may be realized by the ROM 100 shown in FIG. 2. Furthermore, this calculating circuit 14 may be alternatively realized by employing logic circuitry shown in FIG. 5.

Figure 5:
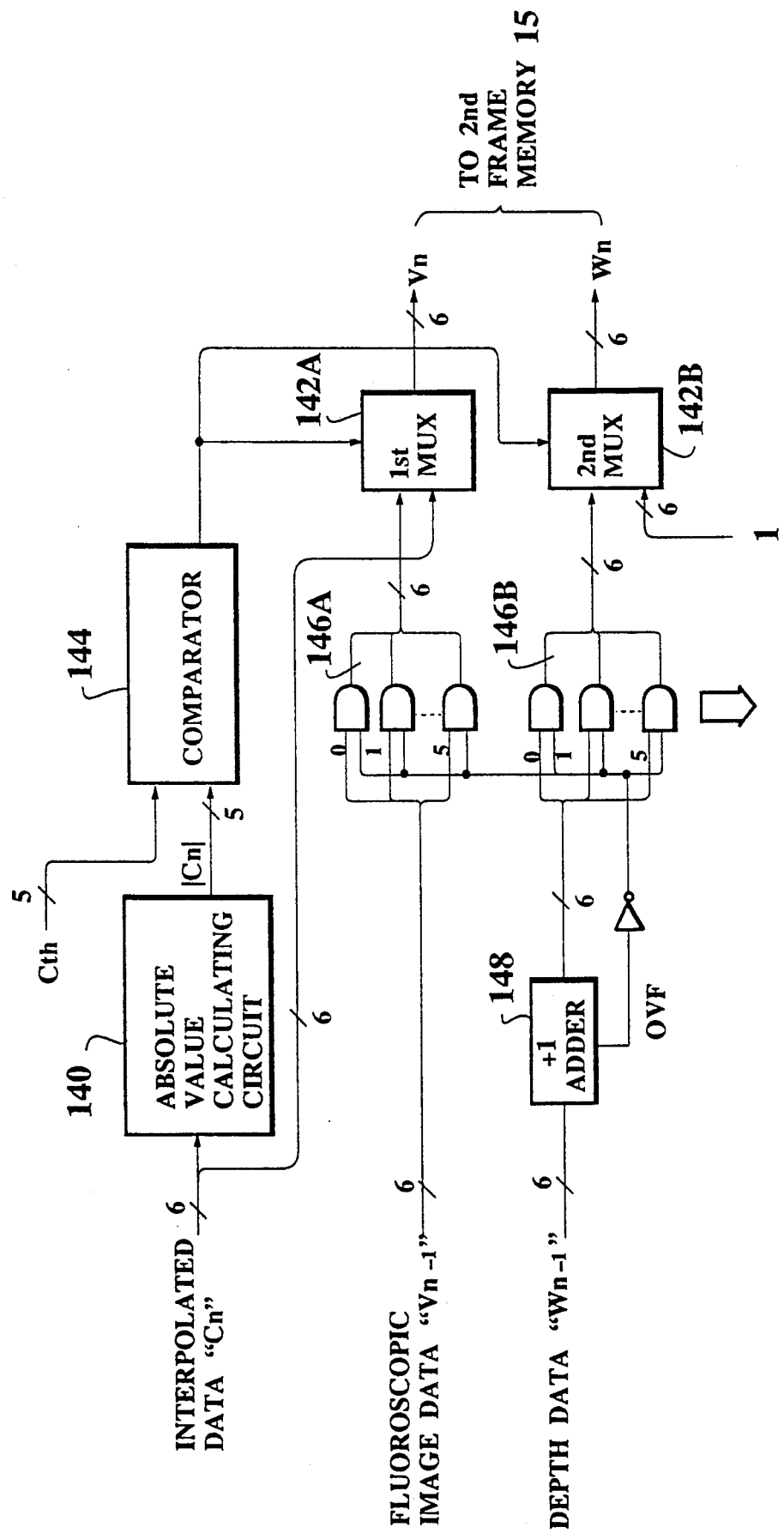
FIG. 5 is a logic circuit diagram of the angiographic data calculating circuit 14 shown in FIG. 3 as a modification.

In the angiographic data calculating circuit 14 constructed of the logic circuitry represented in FIG. 5, the interpolated data "$C_n$" having 6 bits is supplied from the interpolation calculating circuit 12 of FIG. 4 to an absolute value calculating circuit 140 and a first multiplexer 142A. Then, an absolute value of the interpolated data $|C_n|$ is calculated in the absolute value calculating circuit 140. This absolute value $|C_n|$ is supplied to one input terminal of a comparator 144 having another input terminal to which the above-described noise removing parameter is supplied. Then, the comparison result of the comparator 144 (namely, absolute value "$C_n$" < parameter $C_{th}$) is supplied to the first multiplexer 142A and also to a second multiplexer 142B.

On the other hand, the fluoroscopic image data of the preceding frame "$V_{n-1}$" is supplied to a first AND gate unit 146A, and an output of the first AND gate unit 146A is supplied to the first multiplexer 142A, so that this AND gate bloodflow velocity data "$V_{n-1}$" and the interpolated data "$C_n$" are multiplexed with the comparison result in the first multiplexer 142A to produce the fluoroscopic image data of the present frame "$V_n$". This present fluoroscopic image data "$V_n$" is then written into the second frame memory 15. Similarly, the depth data of the preceding frame "$W_{n-1}$" is inputted into an adder 148 so that 1 is added to this depth data. The added depth data is supplied to a second AND gate unit 146B. An overflow bit "OVF" is also supplied from the adder 148 to this second AND gate unit 146B, so that if the added depth data ($W_{n-1}+1$) from the adder 148 exceeds "63", then both of the data "$W_n$" and "$V_n$" are set to "0". The output from the second AND gate unit 146B is supplied to the second multiplexer 142B to which "1" is also supplied. As a result, the depth data "$W_n$" of the present frame is outputted from the second multiplexer 142B and then is written into the second frame memory 15.

DATA REPRESENTATION

The above-described B-mode data, fluoroscopic image (V) data and angiographic image data are represented in display regions shown in FIG. 6 of the color monitor 7E.

Figure 6A:
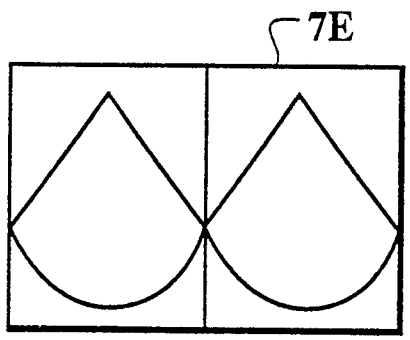
FIG. 6A to 6D are various display conditions of the first ultrasonic imaging system shown in FIG. 3.

For instance, as shown in FIG. 6A, the B-mode data are used to display the identical ultrasonic B-mode images in a real time mode on both of a right-half portion and a left-half portion of a display screen of the color monitor 7E.

Figure 6B:
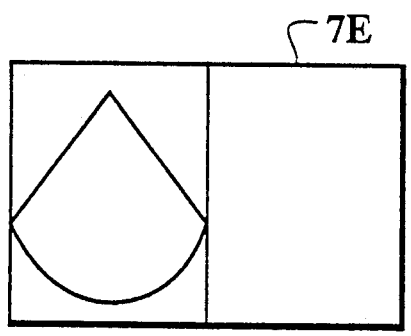

The fluoroscopic image (V) data is used to display a fluoroscopic image on the left-half screen portion, as shown in FIG. 6B.

Figure 6C:
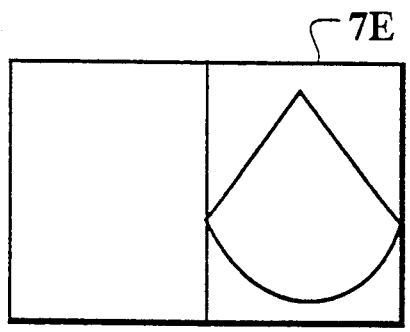

The angiographic image data is used to display an angiogram on the right-half screen portion, as represented in FIG. 6C.

Figure 6D:
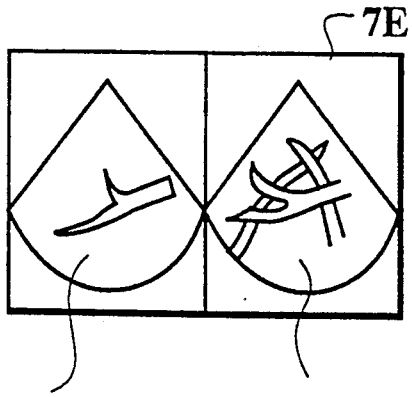

In the color data processing circuit 7C, the above-described three different sorts of data are superimposed, so that one image produced by combining the B-mode data with the fluoroscopic image data is represented on the left-half screen, whereas the other image produced by combining the B-mode data with the angiographic image data is represented on the right-half screen, as shown in FIG. 6D.

INTERNAL ARRANGEMENT OF COLOR DATA PROCESSING CIRCUIT

Figure 7:
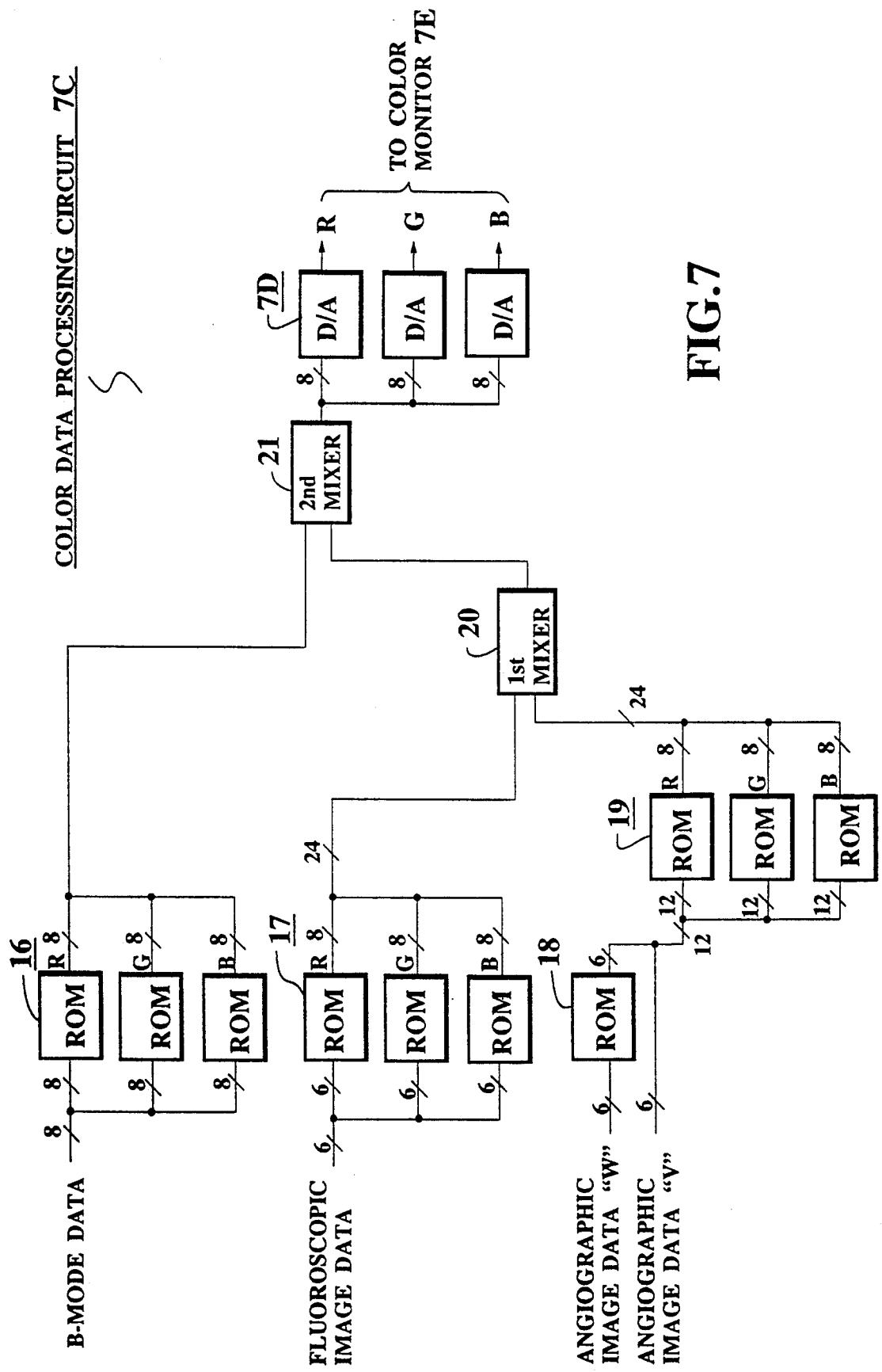
FIG. 7 is an internal circuit arrangement of the color data processing circuit 7C shown in FIG. 3.

FIG. 7 is an internal circuit arrangement of the color data processing circuit 7C of FIG. 3. The color data processing circuit 7C includes a first coloring ROM group 16 for coloring the B-mode image, a second coloring ROM group 17 for coloring the fluoroscopic image, a ROM 18 for converting the non-linear gradation of the angiographic image (depth data) "W", a third ROM group 19 for coloring the angiographic images "W" and "V", and first/second mixers 20 and 21. To the output of the second mixer 21, three sets of A/O converters 7D are connected, so that these color-processed data are converted into R.G.B. color image signals. These R.G.B. color image signals are supplied to the color monitor 7E.

In the first coloring ROM group 16 of the color data processing circuit 7C, such a process is performed to represent the B-mode image of the biological body 50 under medical examination in the monochrome mode. It should be noted that when there is either the fluoroscopic image (V) data, or the angiographic image data at the same pixel, either the fluoroscopic image, or the angiographic image is represented with a top priority with respect to the B-mode image.

Figure 8A:
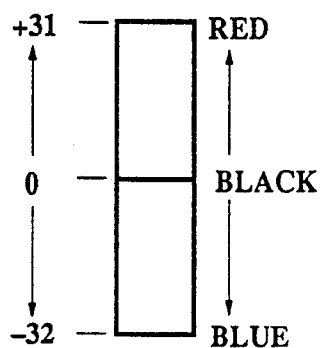
FIGS. 8A to 11 represent various color display modes of the first ultrasonic imaging system shown in FIG. 3.
Figure 8B:
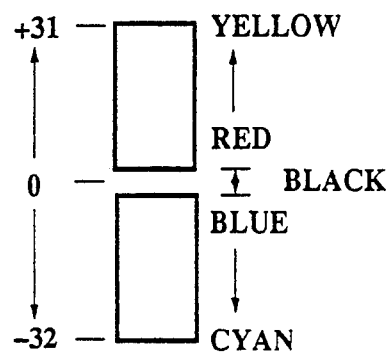

In the second coloring ROM group 17, such a coloring operation as shown in FIGS. 8A and 8B is performed in accordance with the fluoroscopic image data.

In the third coloring ROM group 19, such a coloring process operation is carried out with respect to the angiographic image data that both of the three-dimensional position information "W" and the latest velocity information "V" are simultaneously displayed, and otherwise only the three-dimensional position information "W" is displayed.

Figure 9:
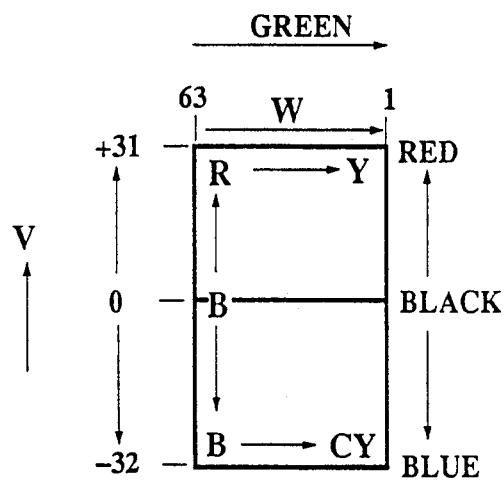

First, when both of the 3-D position information "W" and the velocity information "V" are displayed at the same time, the coloring operation is performed as shown in FIG. 9. That is, with respect to the direction/velocity of the bloodflow, the coloring operation as represented in FIG. 8A is carried out. Furthermore, a green component is added to this coloring operation in order to represent the 3-D position information.

Figure 10:
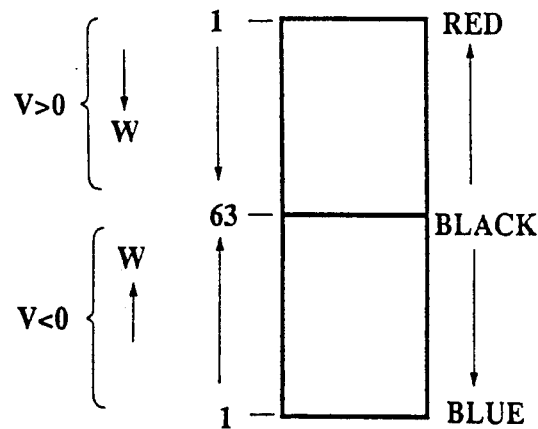

If a viewer wants to observe only a 3-D structure of a blood vessel without bloodflow information, only the representation of the 3-D position information "W" is satisfied. Then, in such a coloring operation, only the value of the 3-D position information W and the symbol of the velocity information are used for this coloring operation as shown in FIG. 10.

Figure 11:
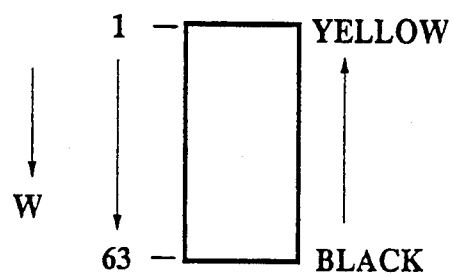

Moreover, if the information about the bloodflow direction is no longer required, a representation of FIG. 11 may be made.

ARRANGEMENT/OPERATION OF SECOND ULTRASONIC IMAGING SYSTEM

As previously explained in the first ultrasonic imaging system shown in FIG. 3, both of the B-mode image data inputted into the B-mode data DSC 7A and the CFM image data inputted into the CFM DATA DSC 7B are the most recent data which are currently obtained by scanning the biological body 50.

To the contrary, there is another possibility in the present invention. That is, in accordance with a second ultrasonic imaging system shown in FIG. 12, there are additionally provided a B-mode data image memory 500 and a CFM data image memory 600. These image memories 500 and 600 have larger memory capacities than those of the above-described frame memories 13 and 15 shown in FIG. 4, and therefore are capable of storing several tens of frame data to several hundreds of frame data. The B-mode image data and the CFM image data are temporarily stored in the respective image memories 500 and 600 during one scanning operation, and these image data are read out from the corresponding image memories 500 and 600 after this scanning operation is accomplished, which will then be processed in the B-mode data DSC 7A, the CFM data DSC 7B and the color data process circuit 7C, so that an angiogram similar to that of the first ultrasonic imaging system may be displayed on the color monitor 7E.

ARRANGEMENTS/OPERATIONS OF THIRD/FOURTH/FIFTH ULTRASONIC IMAGING SYSTEMS

Figure 13:
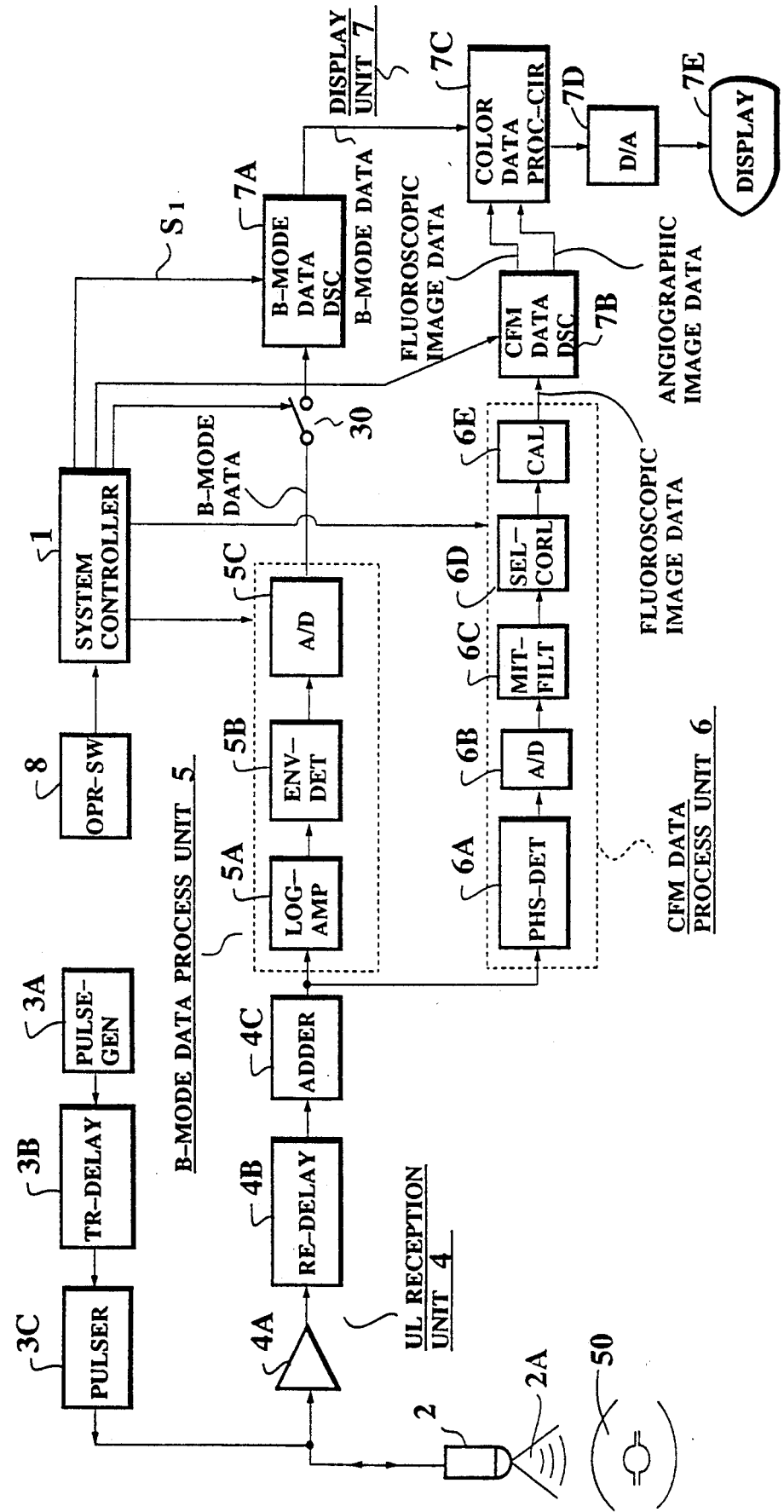
FIG. 13 is a schematic block diagram of a third ultrasonic imaging system according to the present invention.

FIG. 13 shows an overall arrangement of a third ultrasonic imaging system according to the present invention. As apparent from this arrangement of FIG. 13, the major circuit arrangement of the third ultrasonic imaging system is very similar to that of the first ultrasonic imaging system shown in FIG. 3. A switch 30 is newly interposed between the A/D converter 5C of the B-mode data process unit 5 and the B-mode data DSC 7A.

The above-described third ultrasonic imaging system represented in FIG. 13 is operated as follows:

As previously stated, the B-mode image superimposed on the angiogram always corresponds to such an image of the most recent frame data in the first ultrasonic imaging system. Alternatively, other types of B-mode images may be superimposed on an angiogram in the third ultrasonic imaging system. For instance, when the operation switch 8 is operated, only the B-mode image data acquired at this switch operation is temporarily stored in, for instance, a memory (not shown in detail) of the B-mode data DSC 7A and also the subsequent B-mode image data produced after this switch operation are prohibited to be written into this memory by opening the switch 30. Then, only a B-mode image produced from the B-mode image data stored in this memory may be superimposed on the angiogram.

Figure 14A:
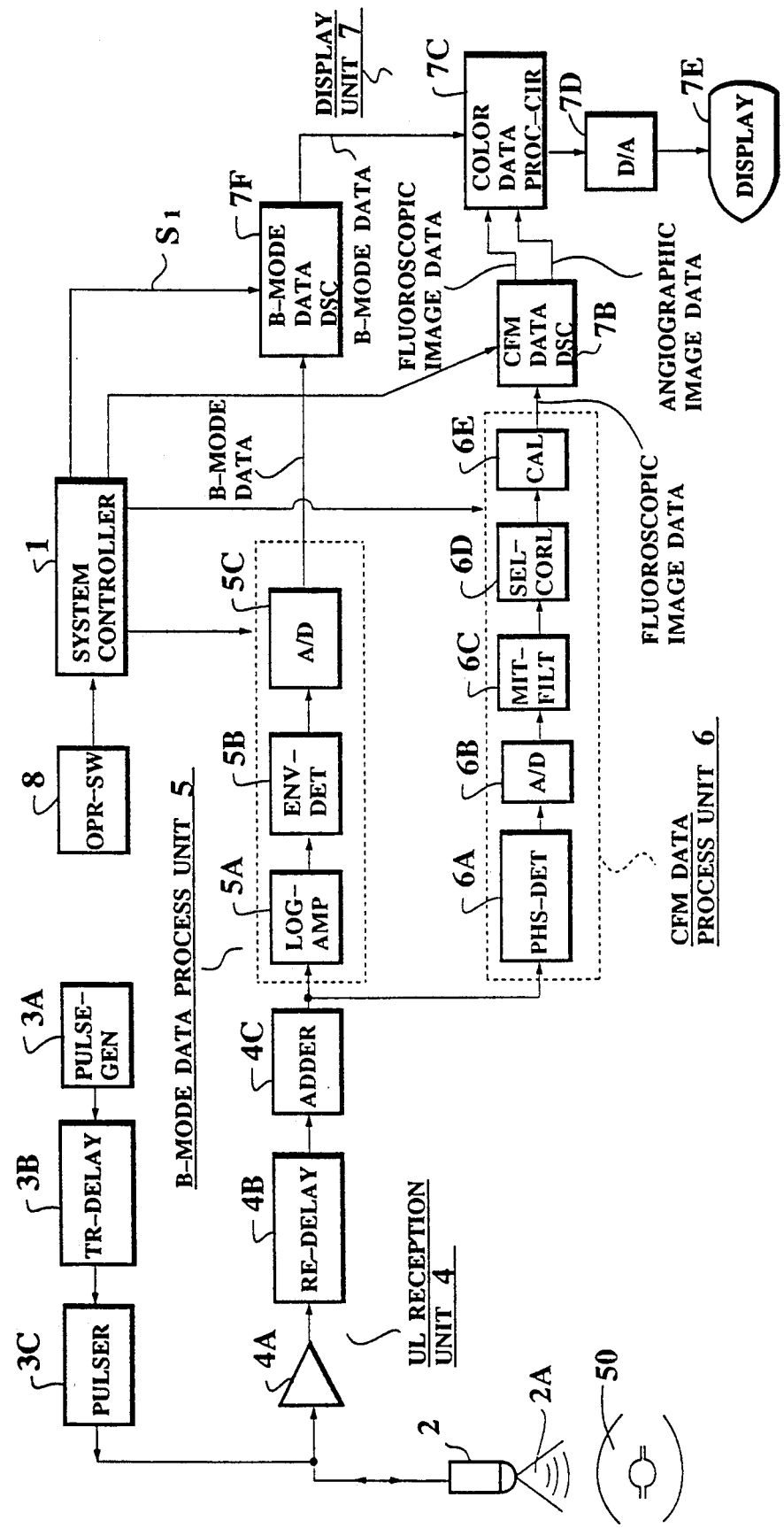
FIG. 14A is a schematic block diagram of a fourth ultrasonic imaging system according to the present invention.
Figure 14B:
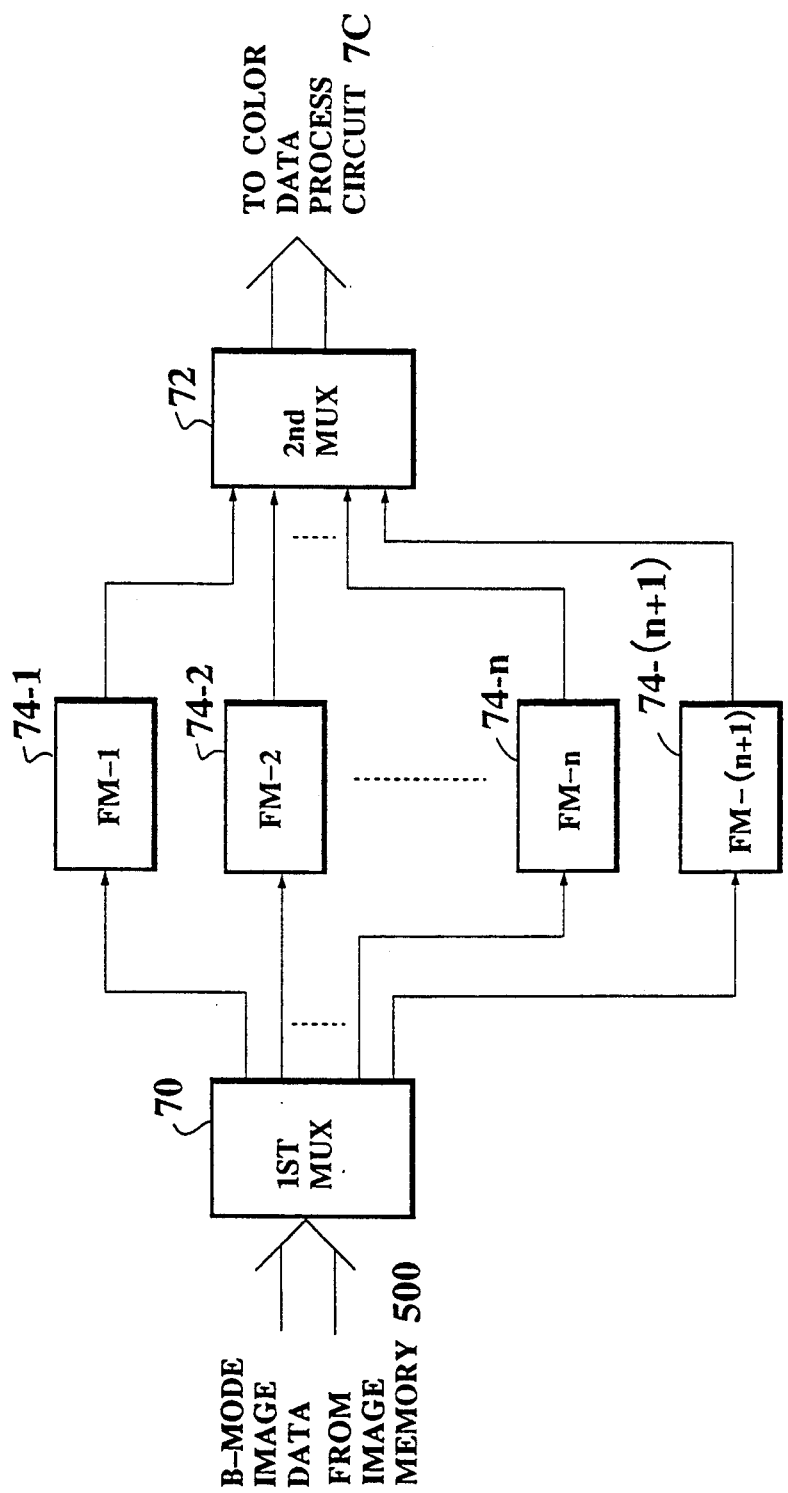
FIG. 14B is an internal circuit diagram of the B-mode data DSC 7F shown in FIG. 14A.

FIG. 14A shows an overall arrangement of a fourth ultrasonic imaging system according to the present invention. In this fourth ultrasonic imaging system, instead of the B-mode data DSC 7A of the first ultrasonic imaging system shown in FIG. 3, a B-mode data DSC 7F as represented in FIG. 14B is employed. In this new B-mode data DSC 7F, "n+1" pieces of frame memories 74-1 to 74-(n+1) are connected between a first multiplexer 70 and a second multiplexer 72. It should be noted that symbol "n" denotes any integer larger than 2.

Then, the B-mode image data acquired during one scanning operation of the ultrasonic probe 2 over the biological body 50 under medical examination are outputted from the A/D converter 5C of the B-mode data process unit 8, and thereafter are supplied via the first multiplexer 70 to the corresponding frame memories 74-1 to 74-(n+1) so as to be stored therein.

Once all of these frame memories 74-1 to 74-(n+1) are stored with the B-mode image data, the second multiplexer 72 is operated to read out only one B-mode image data from, for instance, the first frame memory 74-1 under control of the system controller 1. As a consequence, the B-mode images acquired before "n" frames within the respective scanning operations are superimposed on the real-time angiogram.

Figure 15A:
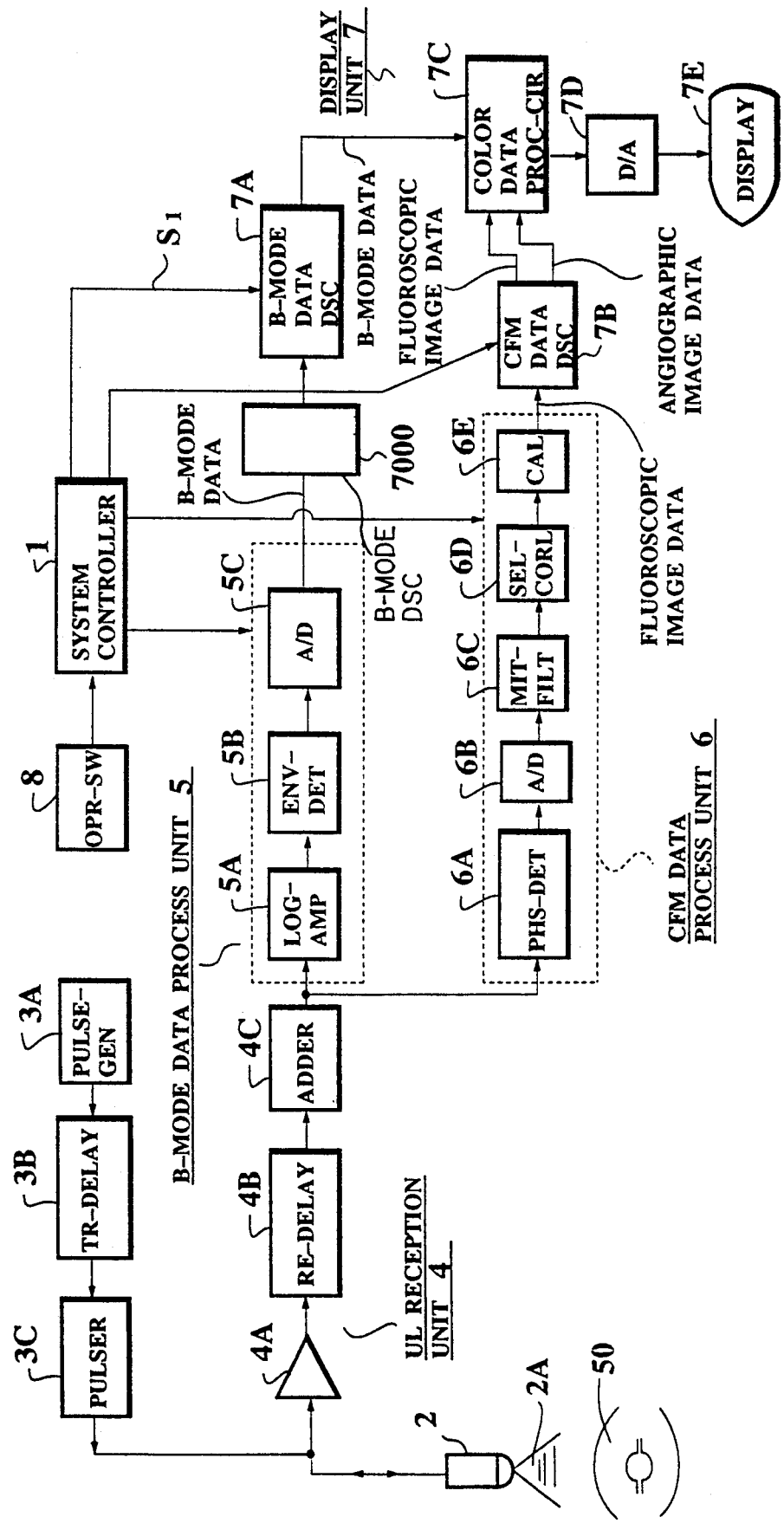
FIG. 15A is a schematic block diagram of a fifth ultrasonic imaging system according to the present invention.
Figure 15B:
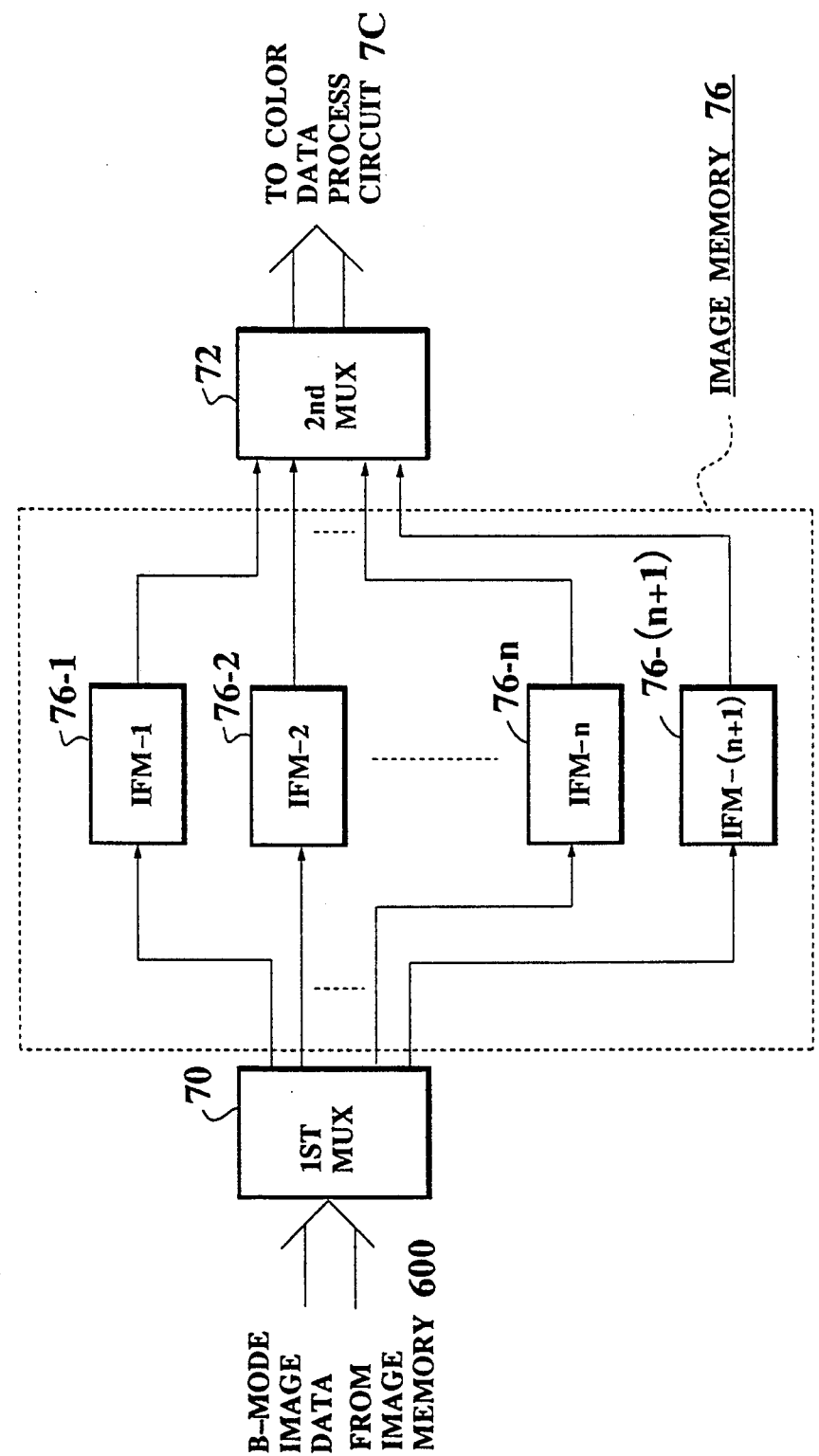
FIG. 15B is an internal circuit diagram of the B-mode data image memory unit 7000 shown in FIG. 15B.

Similarly, FIG. 15A represents an overall arrangement of a fifth ultrasonic imaging system according to the present invention, and FIG. 15B shows an internal circuit arrangement of a B-mode data image memory unit 7000 employed in this fifth ultrasonic imaging system. In this B-mode data image memory unit 7000, a single image memory 76 having "n+1" pieces of frame memory regions IFM-1 to IFF-(n+1) is employed. Since the storage operation and read operation of the B-mode image data are similar to those of the B-mode data DSC 7F shown in FIG. 14B, no further explanation is made in the specification.

As apparent from the first ultrasonic imaging system, the calculating circuit 6E employed in the CFM data process unit 6 in each of the second to fifth ultrasonic imaging systems may be realized by either the ROM 100 of the IIR digital filter 1000 shown in FIG. 2, or the logic circuitry shown in FIG. 5.

ARRANGEMENT/OPERATION OF SIXTH ULTRASONIC IMAGING SYSTEM

FIG. 16 represents an overall arrangement of a sixth ultrasonic imaging system according to the present invention.

A major feature of this sixth ultrasonic imaging system is as follows. The ultrasonic probe 2 is positionally controlled within a three-dimensional region and positional data with respect to this probe 2 is detected by a position detector 9. This positional data of the probe 2 is processed in a CFM data DSC (digital scan converter) 7H, so that positional shifts of a blood vessel displayed on an ultrasonic B-mode image can be corrected based upon the positional data.

Figure 17:
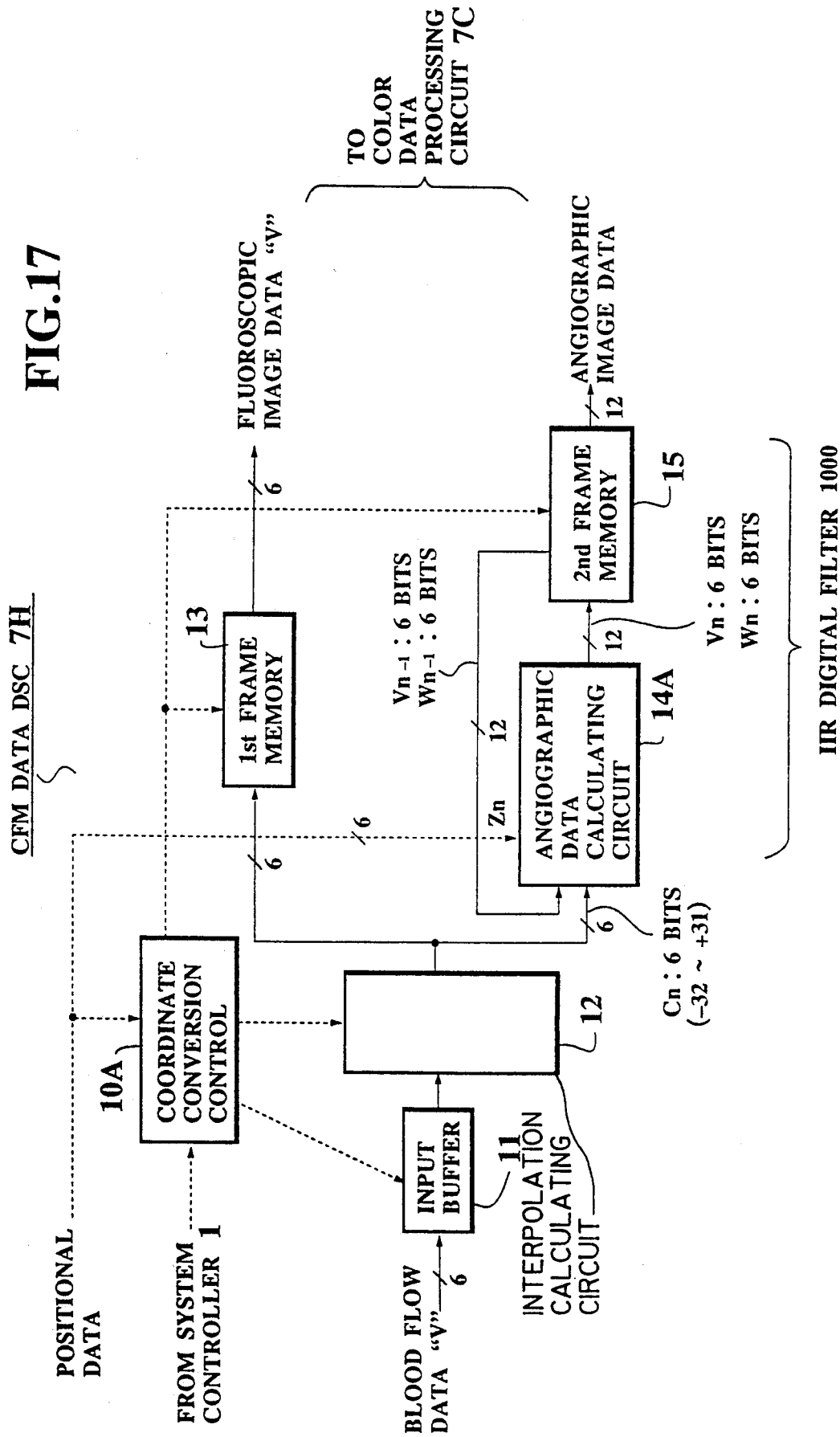
FIG. 17 is an internal circuit diagram of the CFM data DSC 7H shown in FIG. 16.

The positional data detected by the position detector 9 is supplied to a coordinate conversion control circuit 10A and also to an angiographic data calculating circuit 14A as represented in FIG. 17. Accordingly, the below-mentioned algorithmic process is carried out in this angiographic data calculating circuit 14A, assuming now that the positional data is given as "$Z_n$" having 6 bits (1 to 63):

```
if abs |Cn| ≧ Cth and Zn ≧ Wn−1
then
    Vn = Cn
    Wn = Zn
else
    Vn = Vn−1
    Wn = Wn−1
endif
(initial values: Vo = Wo = 0)
```

Figure 18:
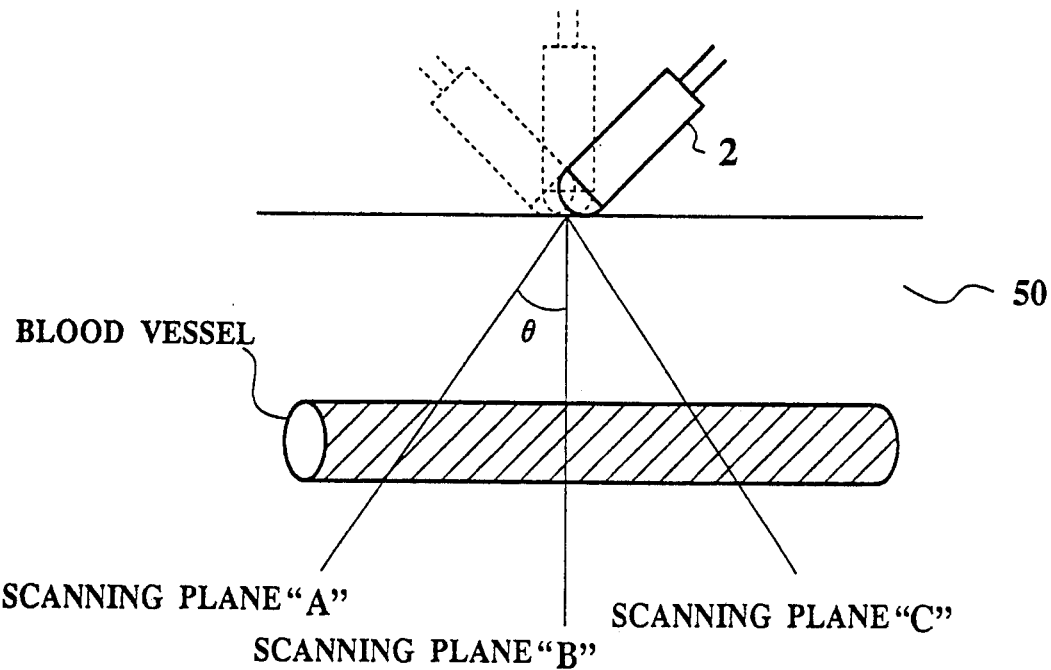
FIGS. 18 and 19 represent how to correct the positional shift appearing in the images of the different scanning planes according to the sixth ultrasonic imaging system of FIG. 16.
Figure 19:
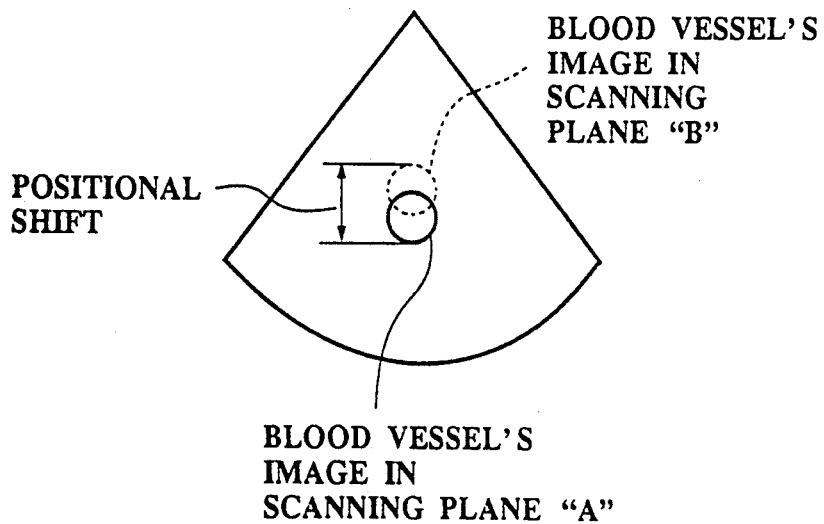

On the other hand, when the ultrasonic probe 2 is moved along a direction intersecting three scanning planes "A", "B", and "C" as represented in FIG. 18, a positional shift or error shown in FIG. 19 is originally caused. However, according to the coordinate conversion control circuit 10A of the sixth ultrasonic imaging system shown in FIG. 17, such a positional shift between the images of the blood vessel, as illustrated in FIG. 19, can be corrected based upon the above-described positional data.

Figure 20:
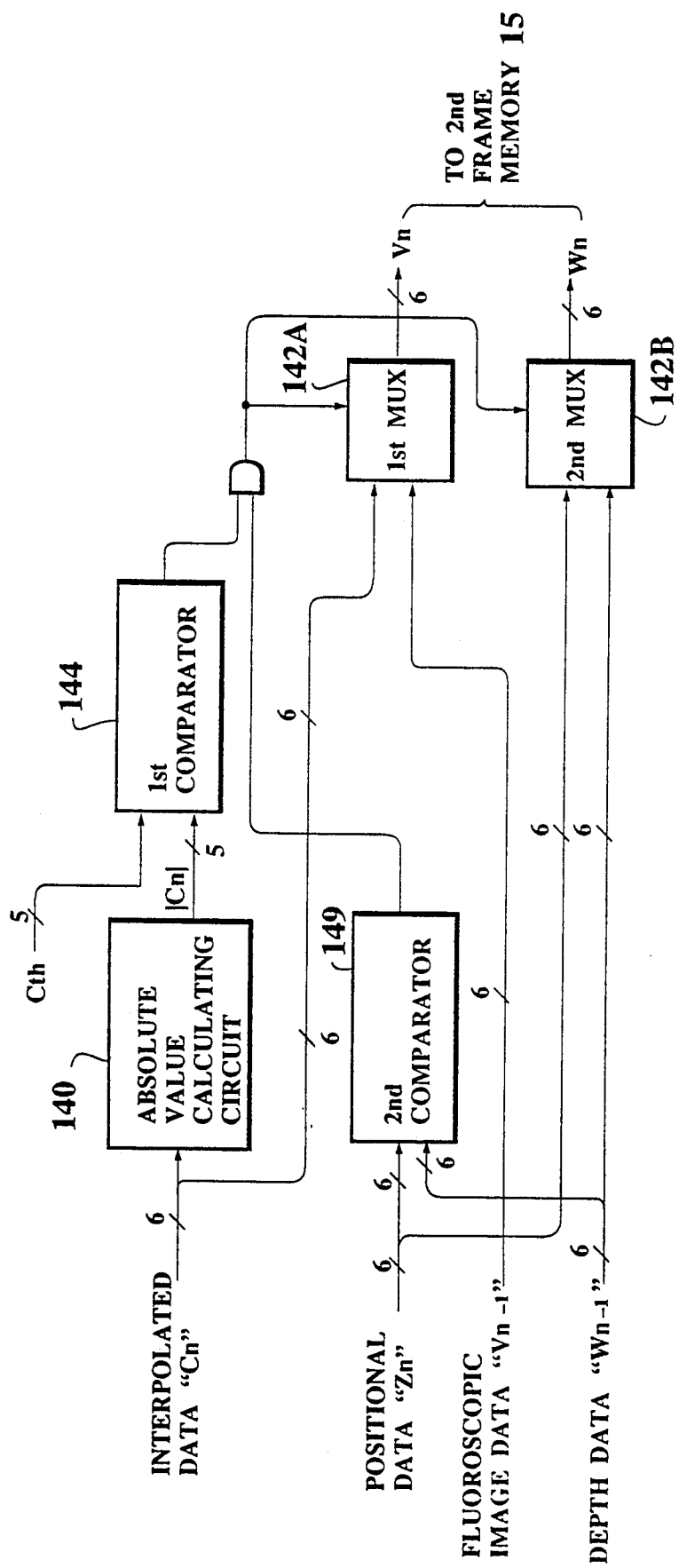
FIG. 20 is an internal circuit diagram of the angiographic data calculating circuit 14A shown in FIG. 17.

The above-described angiographic image data calculating circuit 14A may be similarly realized by the ROM 100 of the IIR digital filter 1000 shown in FIG. 2, or a logic circuit shown in FIG. 20 in which a second comparator 149 is newly employed, and the AND gate groups 146A, 146B and the adder 148 are omitted, as compared with the logic circuit shown in FIG. 5.

ARRANGEMENT/OPERATION OF SEVENTH ULTRASONIC IMAGING SYSTEM

Figure 12:
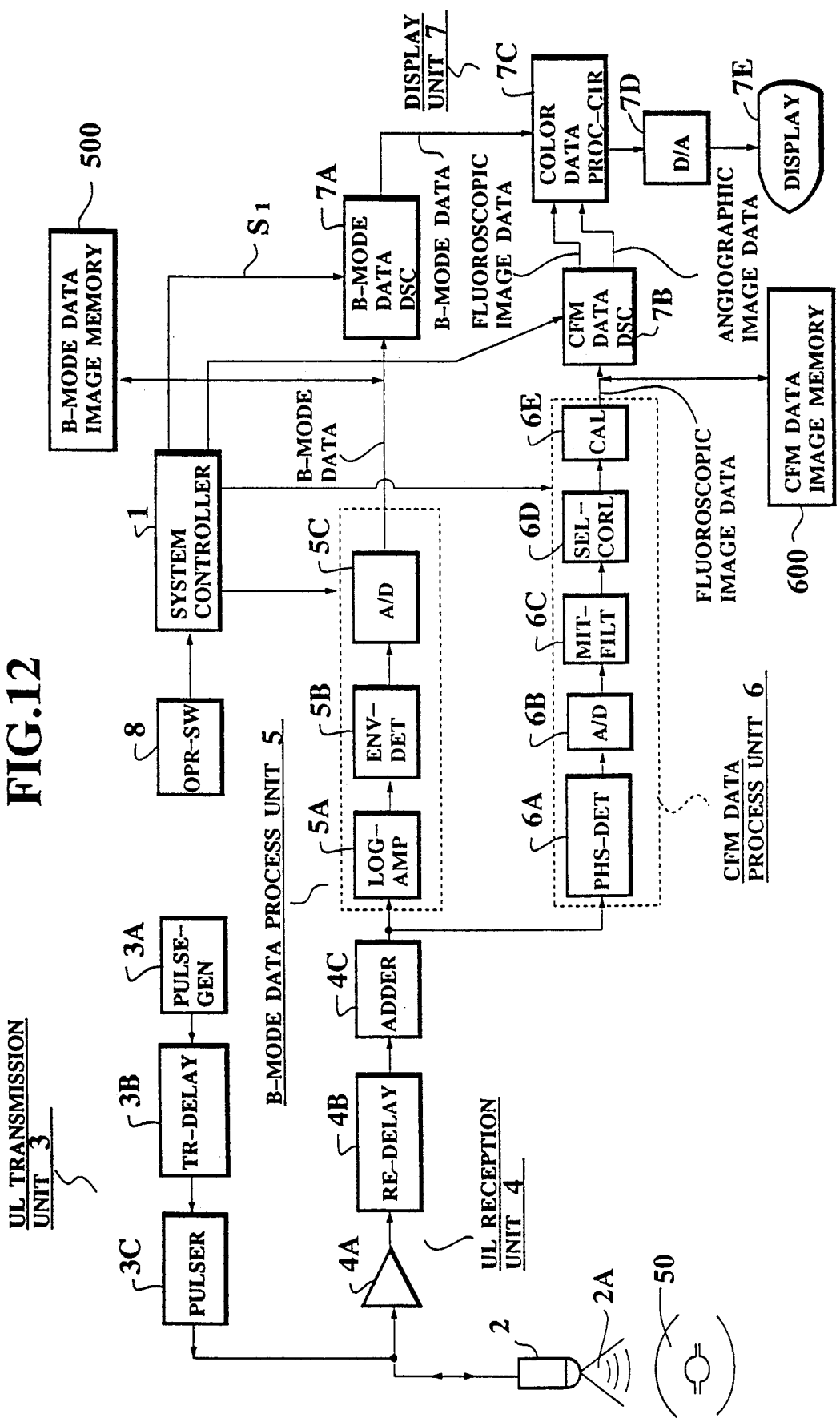
FIG. 12 is a schematic block diagram of a second ultrasonic images system according to the present invention.
Figure 21:
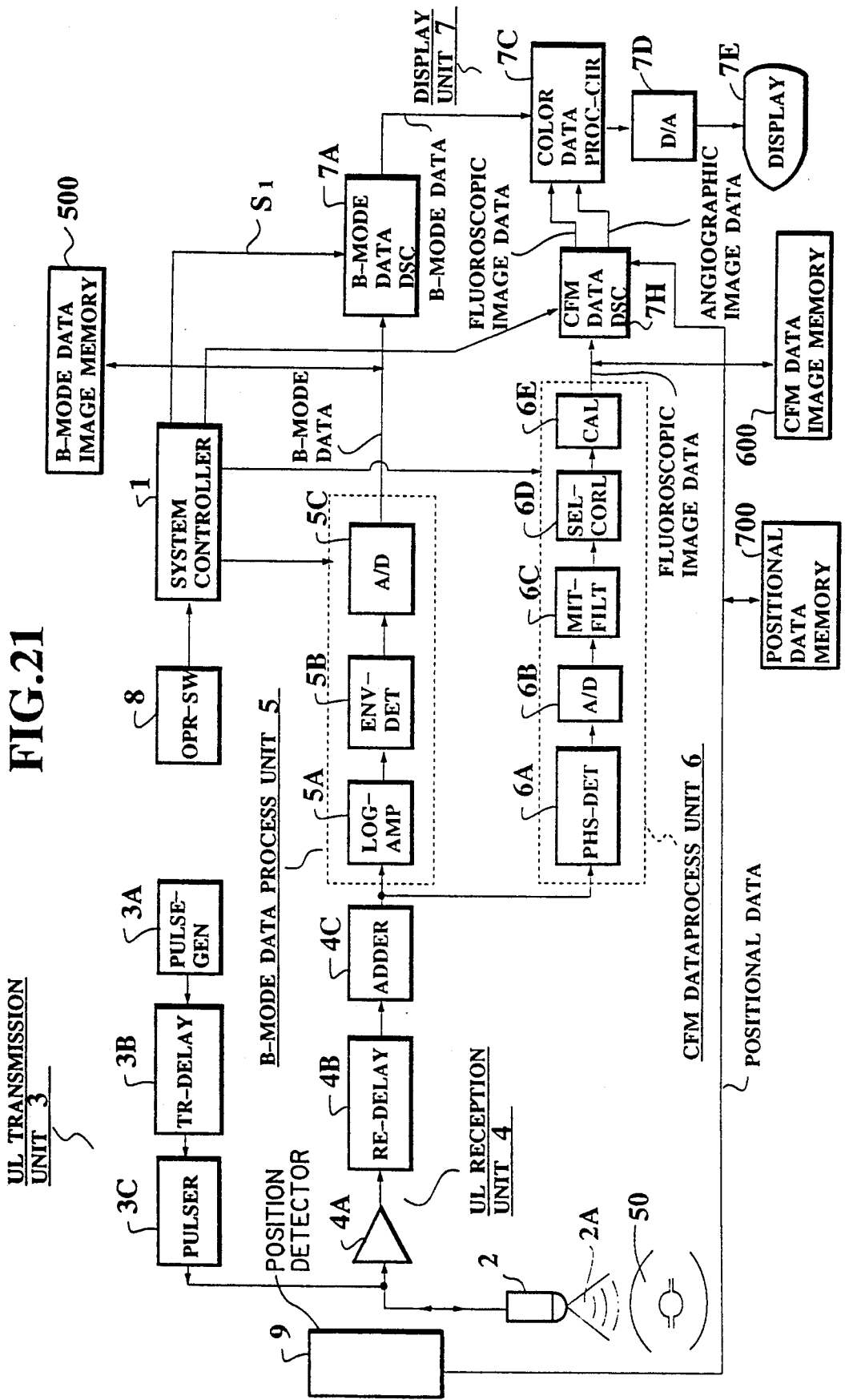
FIG. 21 is a schematic block diagram of a seventh ultrasonic imaging system according to the present invention.

FIG. 21 shows an overall arrangement of a seventh ultrasonic imaging system according to the present invention. As apparent from FIG. 21, a positional data memory 700 and the above-explained B-mode data image memory 500 and CFM data image memory 600 shown in FIG. 12 are newly employed in the arrangement of the sixth ultrasonic imaging system indicated in FIG. 16.

The positional data memory 700 stores the positional data with respect to each of the images of the B-mode/CFM data image memories 500 and 600. As a consequence, after the scanning operation has been completed, the B-mode image is superimposed on the angiographic image (angiogram) which has been produced from the CFM image data positionally corrected in the CFM data DSC 7H.

ARRANGEMENTS/OPERATIONS OF EIGHTH TO ELEVENTH ULTRASONIC IMAGING SYSTEMS

Figure 22:
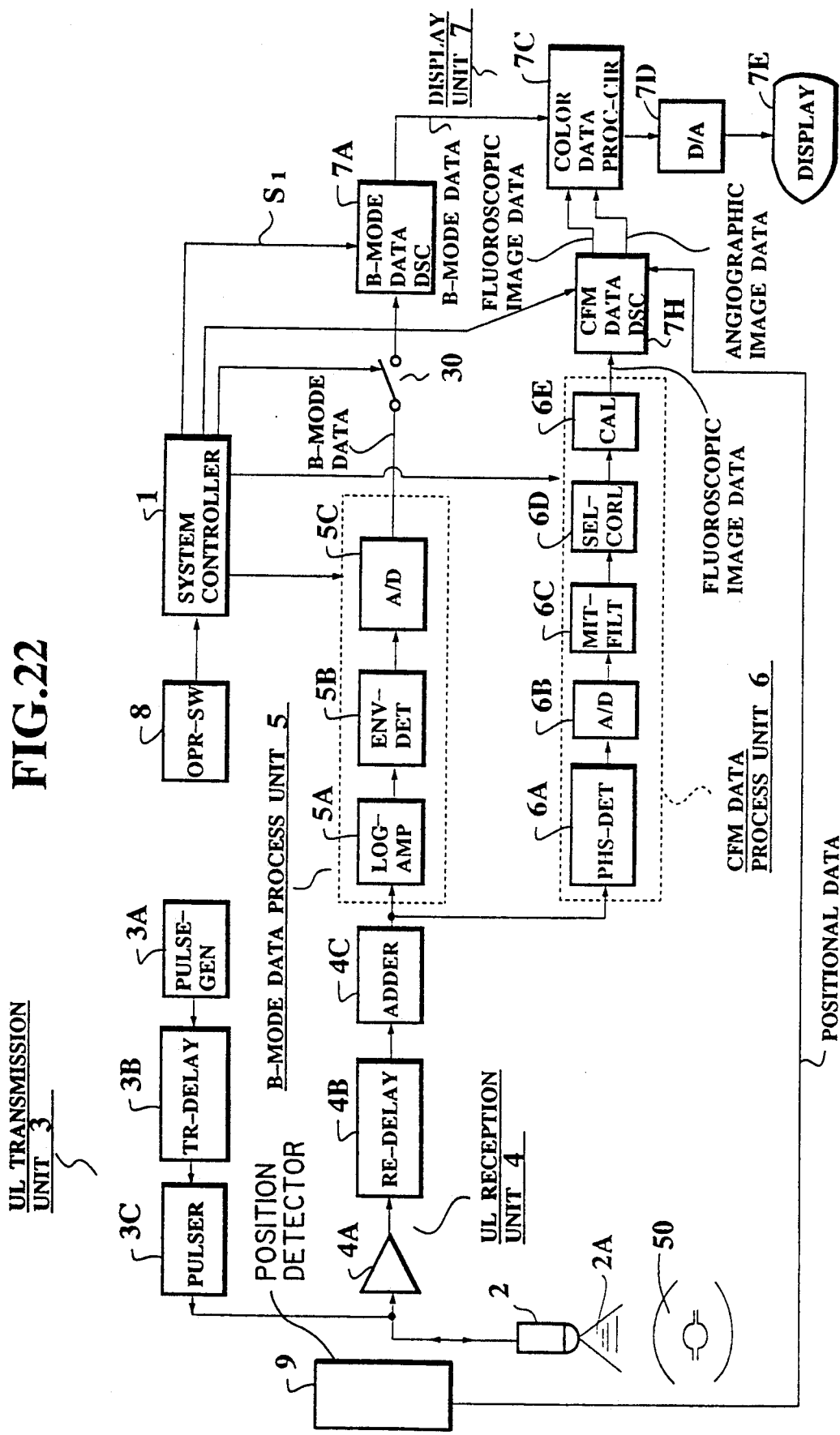
FIG. 22 is a schematic block diagram of a eighth ultrasonic imaging system according to the present invention.

FIG. 22 shows an overall arrangement of an eighth ultrasonic imaging system according to the present invention, which is constructed by combining the sixth ultrasonic imaging system of FIG. 16 with the third ultrasonic imaging system of FIG. 13.

Figure 23:
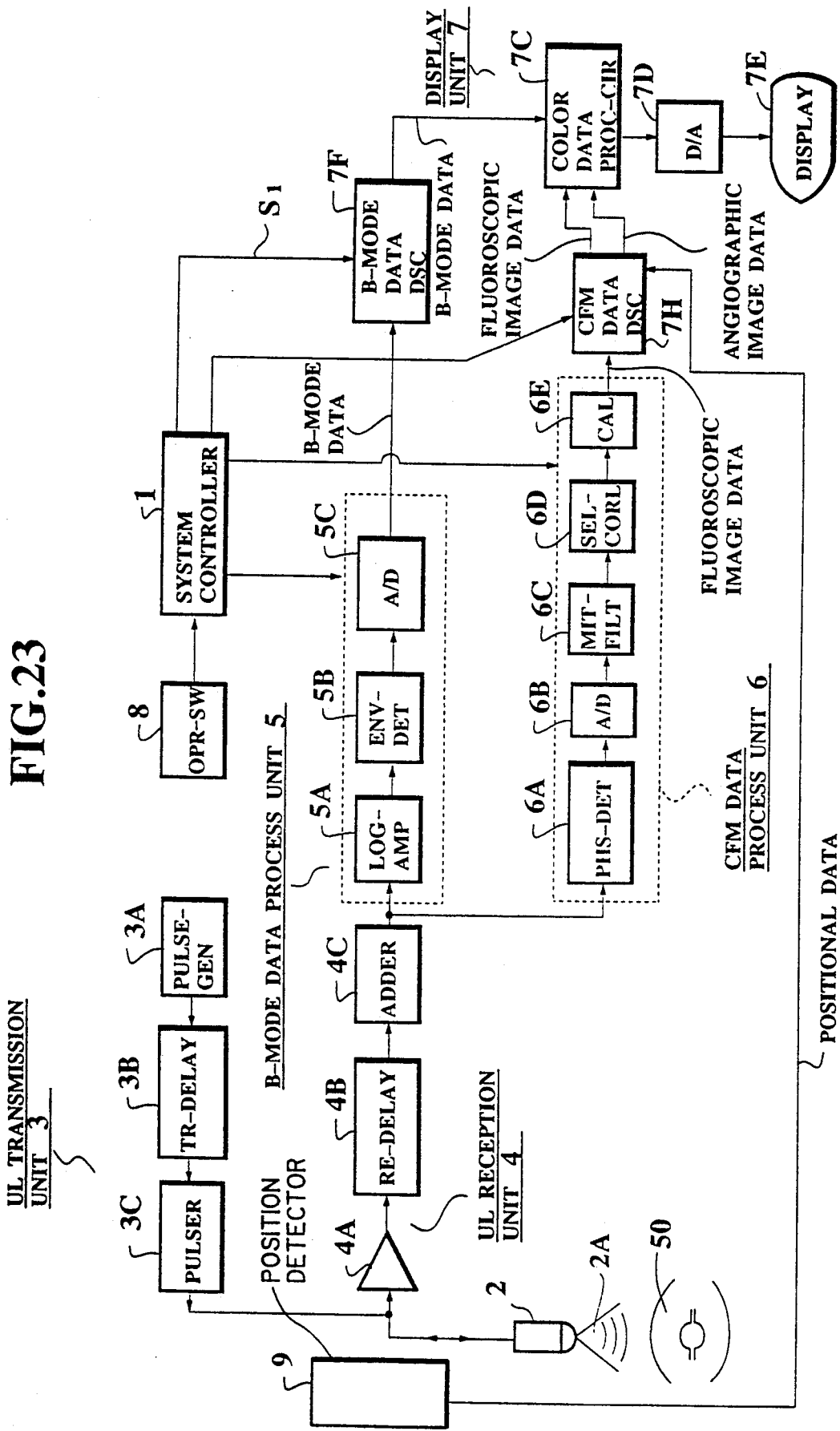
FIG. 23 is a schematic block diagram of a ninth ultrasonic imaging system according to the present invention.

FIG. 23 represents an overall arrangement of a ninth ultrasonic imaging system according to the present invention, which is arranged by combining the sixth ultrasonic imaging system of FIG. 16 with the fourth ultrasonic imaging system shown in FIG. 14A.

Figure 24:
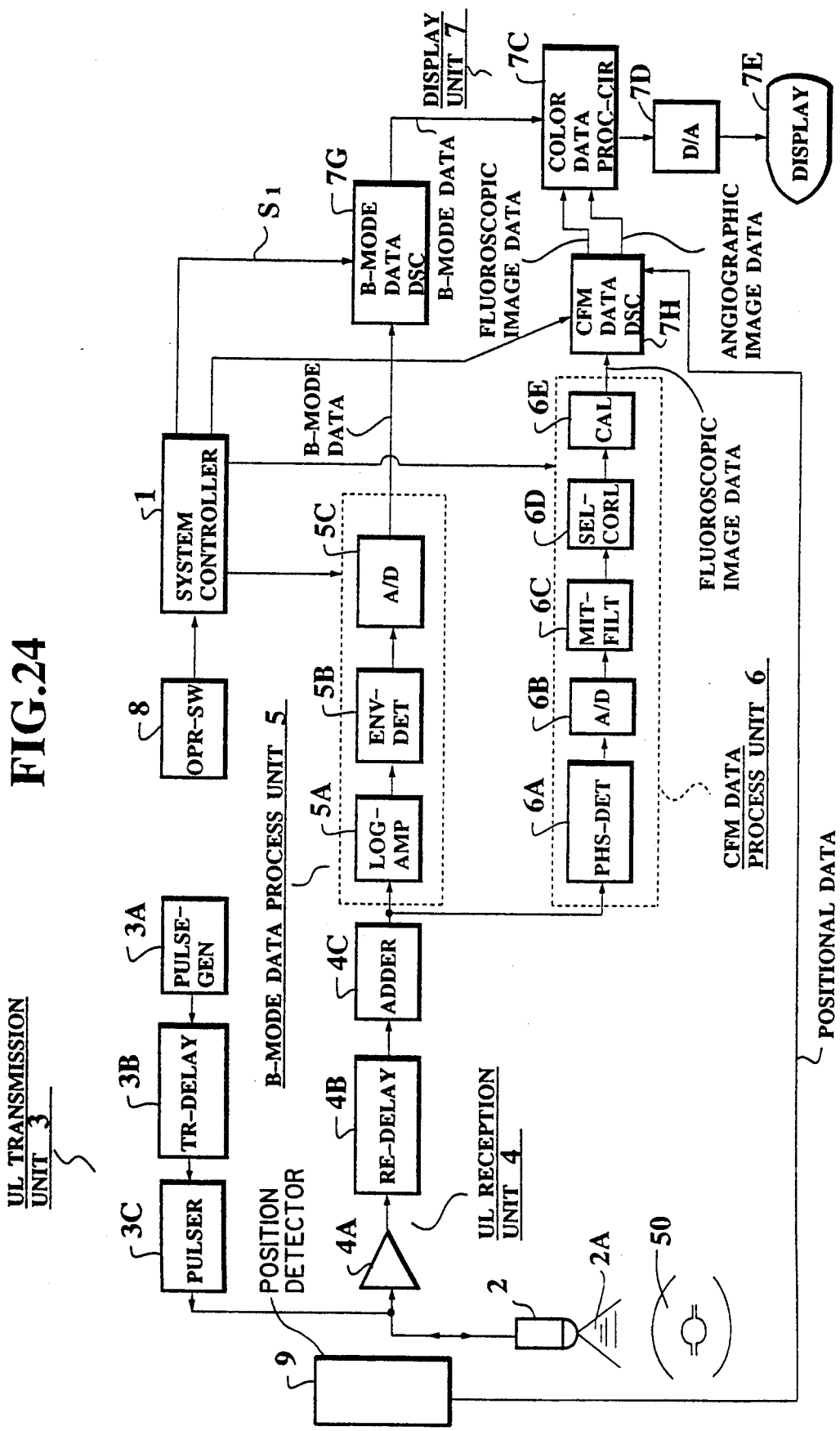
FIG. 24 is a schematic block diagram of a tenth ultrasonic imaging system according to the present invention.

FIG. 24 indicates an overall arrangement of a tenth ultrasonic imaging system according to the present invention, which is constructed by combining the sixth ultrasonic imaging system of FIG. 16 with the fifth ultrasonic imaging system of FIG. 15A.

Since operations of these eighth to tenth ultrasonic imaging systems are essentially the same as those of the combined original ultrasonic imaging systems, no further description is made.

Figure 25:
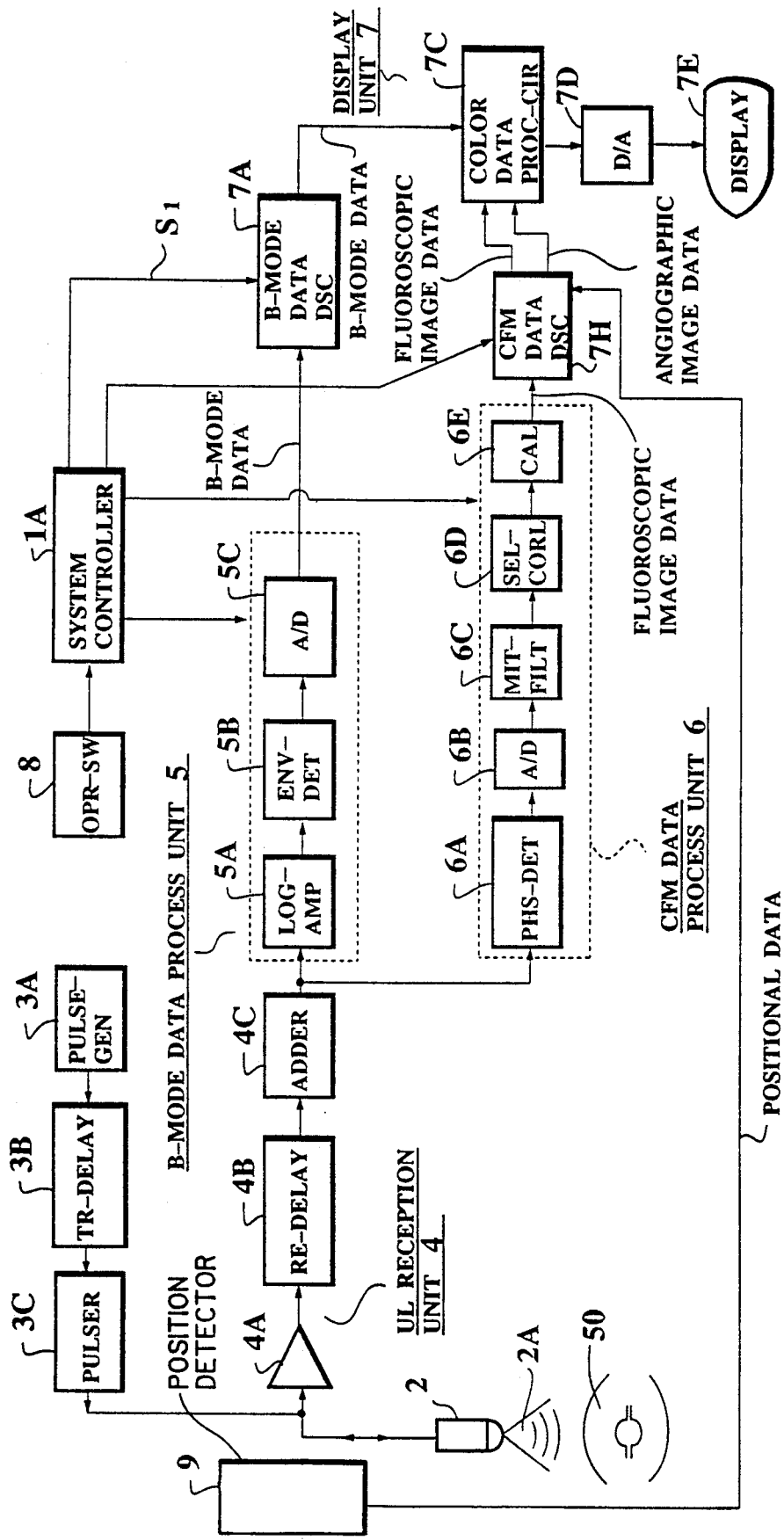
FIG. 25 is a schematically block diagram of an eleventh ultrasonic imaging system according to the present invention.

FIG. 25 shows an overall arrangement of an eleventh ultrasonic imaging system according to the present invention.

In accordance with the eleventh ultrasonic imaging system of FIG. 25, a representation of a B-mode image is previously determined at a preselected scanning position by way of a system controller 1A. Only when the scanning operation by the ultrasonic probe 2 is performed at this preselected scanning position, the B-mode image data from the A/D converter 5C is written into the memory (not shown in detail) of the B-mode data DSC 7H. Accordingly, the B-mode image acquired at the preselected scanning position can be superimposed on the angiogram.

MODIFICATIONS

The present invention is not limited to the above-described preferred embodiments, but may be modified without departing from the technical scope of the present invention.

For instance, when there exist many blood vessels, if an angiographic image is produced from a large quantity of images containing these blood vessels, the resultant image is filled with the blood vessel's images, so that the B-mode image is obscured. As a result, it is difficult to observe a medical/biological relationship between the blood vessels and the B-mode image. In such a case, the number of frames to be three-dimensionally synthesized may be reduced by the ROM 18 of the color data processing circuit 7C shown in FIG. 7, so that only the blood vessel image close to the B-mode image may be displayed. That is, when the point where the output W'=0 by the ROM 18 is synthesized with the B-mode data in the second mixer 21, the B-mode image is displayed. To the contrary, in case of W' being not equal to 0, the angiogram is displayed. Similar process operations may be applied to the frozen image data after the scanning operation is completed, so that the number of synthesized frames to be displayed may be varied and the coloring process by "W" may be changed.

Figure 26:
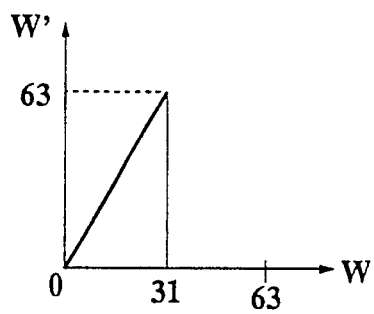
FIGS. 26 and 27 are graphic representations for explaining modifications of the present invention.
Figure 27:
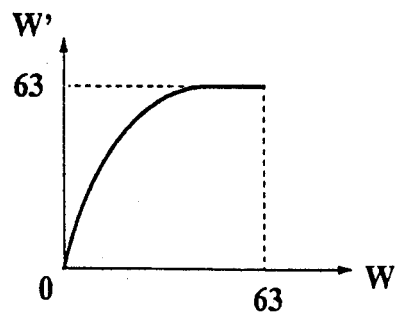

Also, before displaying "W", when a non-linear gradation conversion is carried out in the above-described ROM 18, a range of an angiogram signal component may be narrowed to, for example, 64/2 frames as shown in FIG. 25. Also, as shown in FIG. 26, the coloring process of "W" may be varied in order to emphasize 3D-representation conditions of the new frame.

It should be noted that each of the above-described modification processes is performed without any positional detection. The angiogram is so arranged by synthesizing 64 frames acquired from the present frame to 63 preceding frames. Then, the angiogram representation is performed by overlapping the most recent frame on the preceding frames, and the sector scanning operation is carried out.

As a consequence, according to the present invention, the ultrasonic fluoroscopic imaging operation equivalent to the X-ray fluoroscopic imaging operation can be achieved with very simple circuit arrangement in a real time mode.

What is claimed is:

1. An ultrasonic imaging system comprising:
   scanning means for scanning a biological body under medical examination within a three-dimensional volume by producing a plurality of successive two-dimensional scanning planes involving the biological body by utilizing ultrasonic pulses to obtain echo signals produced from echo pulses reflected from the biological body;

ultrasonic image data producing means for producing a plurality of ultrasonic scanned image data about the scanned biological body with regard to the successive scanning planes in response to said echo signals;

bloodflow-distribution image data producing means for producing a plurality of bloodflow-distribution image data about the scanned biological body with regard to the successive scanning planes in response to said echo signals;

storage means for temporarily storing said plurality of bloodflow-distribution image data, while sequentially updating and superimposing said plural bloodflow-distribution image data with each other during a predetermined scanning period for each scanning plane; and display means for displaying a three-dimensional bloodflow-distribution image superimposed on an ultrasonic scanned image by processing both of said bloodflow-distribution image data read out from said storage means, and said ultrasonic scanned image data.

2. An ultrasonic imaging system as claimed in claim 1, wherein said storage means includes:

an angiographic data calculating circuit for calculating said bloodflow-distribution image data derived from said bloodflow-distribution image data producing means to obtain both of fluoroscopic image data and depth data; and a frame memory for sequentially storing said plurality of fluoroscopic image data and depth data, and for sequentially reading therefrom said plurality of fluoroscopic image data and depth data, thereby producing angiographic image data as said bloodflow-distribution image data.

3. An ultrasonic imaging system as claimed in claim 2, wherein said angiographic data calculating circuit is constructed of logic circuitry including an absolute value calculating circuit 140, first and second multiplexers, a comparator, first and second AND gate groups, and an adder.

4. An ultrasonic imaging system as claimed in claim 1, wherein said storage means is constructed of an IIR (infinite impulse response) digital filter.

5. An ultrasonic imaging system as claimed in claim 4, wherein said IIR digital filter is arranged by a ROM (read-only memory) and a frame memory in such a manner that said plurality of bloodflow-distribution image data are sequentially written and read into/from said ROM and frame memory.

6. The ultrasonic imaging system according to claim 1, wherein a plurality of ultrasonic scanned images are successively acquired from said ultrasonic image data producing means during said predetermined scanning period and said ultrasonic scanned images to be superimposed on said three-dimensional bloodflow-distribution image is the most recent of said successively acquired ultrasonic scanned images.

7. The ultrasonic imaging system according to claim 1, wherein said three-dimensional bloodflow-distribution image is displayed by said display means simultaneously with a two-dimensional color Doppler bloodflow-distribution image, said three-dimensional and two-dimensional bloodflow-distribution images being superimposed on the most recent ultrasonic scanned image of a plurality of ultrasonic scanned images acquired from said ultrasonic image data producing means.

8. An ultrasonic imaging system comprising:

scanning means for scanning a biological body under medical examination within a three-dimensional volume by producing a plurality of successive two-dimensional scanning planes involving the biological body by utilizing ultrasonic pulses to obtain echo signals produced from echo pulses reflected from the biological body;

ultrasonic image data producing means for producing a plurality of ultrasonic scanned image data about the scanned biological body with regard to the successive scanning planes in response to said echo signals;

bloodflow-distribution image data producing means for producing a plurality of bloodflow-distribution image data about the scanned biological body with regard to the successive scanning planes in response to said echo signals;

storage means for temporarily storing said plurality of bloodflow-distribution image data, while sequentially updating and superimposing said plural bloodflow-distribution image data with each other during a predetermined scanning period for each scanning plane; and display means for displaying a three-dimensional bloodflow-distribution image superimposed on an ultrasonic scanned image for processing both of said bloodflow-distribution image data read out from said storage means acquired during said predetermined scanning period and said ultrasonic scanned image data; and means for detecting scanning positions of said scanning means to produce positional data with respect to said scanning planes, whereby said storage means corrects superimposing positions of said plural bloodflow-distribution image data based on said positional data.

9. An ultrasonic imaging system as claimed in claim 8, further comprising:

a first image memory for storing said plurality of ultrasonic scanned image data during said predetermined scanning period;

a second image memory for storing said plurality of bloodflow-distribution image data during said predetermined scanning period; and a positional data memory for storing said positional data during said predetermined scanning period, whereby said storage means sequentially updates and superimposes said plurality of bloodflow-distribution image data with each other read out from said first image memory, and also sequentially corrects said plurality of ultrasonic scanned image data based upon said positional data after a completion of said predetermined scanning period.

10. An ultrasonic imaging system comprising:

scanning means for scanning a biological body under medical examination within a three-dimensional volume by producing a plurality of successive two-dimensional scanning planes involving the biological body by utilizing ultrasonic pulses to obtain echo signals produced from echo pulses reflected from the biological body;

ultrasonic image data producing means for producing a plurality of ultrasonic scanned image data about the scanned biological body with regard to the successive scanning planes in response to said echo signals;

bloodflow-distribution image data producing means for producing a plurality of bloodflow-distribution image data about the scanned biological body with regard to the successive scanning planes in response to said echo signals;

storage means for temporarily storing said plurality of bloodflow-distribution image data, while sequentially updating and superimposing said plural bloodflow-distribution image data with each other during a predetermined scanning period for each scanning plane;

display means for displaying a three-dimensional bloodflow-distribution image superimposed on an ultrasonic scanned image for processing both of said bloodflow-distribution image data read out from said storage means acquired during said predetermined scanning period and said ultrasonic scanned image data;

a first image memory for storing said plurality of ultrasonic scanned image data during said predetermined scanning period; and a second image memory for storing said plurality of bloodflow-distribution image data during said predetermined scanning period, whereby said storage means sequentially updates and superimposes said plurality of bloodflow-distribution image data with each other read out from said first image memory after a completion of said predetermined scanning period.

11. An ultrasonic imaging system comprising:

scanning means for scanning a biological body under medical examination within a three-dimensional volume by producing a plurality of successive two-dimensional scanning planes involving the biological body by utilizing ultrasonic pulses to obtain echo signals produced from echo pulses reflected from the biological body;

ultrasonic image data producing means for producing a plurality of ultrasonic scanned image data about the scanned biological body with regard to the successive scanning planes in response to said echo signals;

bloodflow-distribution image data producing means for producing a plurality of bloodflow-distribution image data about the scanned biological body with regard to the successive scanning planes in response to said echo signals;

storage means for temporarily storing said plurality of bloodflow-distribution image data, while sequentially updating and superimposing said plurality of bloodflow-distribution image data in such a manner that preceding bloodflow-distribution image data is updated/superimposed with present bloodflow-distribution image data; and display means for displaying a three-dimensional bloodflow-distribution image superimposed on an ultrasonic scanned image in a real time mode by processing both of latest bloodflow-distribution image data read out from said storage means, and said ultrasonic scanned image data.

12. An ultrasonic imaging system as claimed in claim 11, wherein said storage means includes:

an angiographic data calculating circuit for calculating said bloodflow-distribution image data derived from said bloodflow-distribution image data producing means to obtain both of calculating image data and depth data; and a frame memory for sequentially storing said plurality of fluoroscopic image data and depth data, and for sequentially reading therefrom said plurality of fluoroscopic image data and depth data, thereby producing angiographic image data as said bloodflow-distribution image data.

13. An ultrasonic imaging system as claimed in claim 12, wherein said angiographic data calculating circuit is constructed of logic circuitry including an absolute value calculating circuit, first and second multiplexers, a comparator, first and second AND gate groups, and an adder.

14. An ultrasonic imaging system as claimed in claim 11, wherein said storage means is constructed of an IIR (infinite impulse response) digital filter.

15. An ultrasonic imaging system as claimed in claim 14, wherein said IIR digital filter is arranged by a ROM (read-only memory) and a frame memory in such a manner that said plurality of bloodflow-distribution image data are sequentially written and read into/from said ROM and frame memory.

16. An ultrasonic imaging system as claimed in claim 11, further comprising:

means interposed between said ultrasonic image data producing means and said display means, for selectively supplying preselected ultrasonic scanned image data from said producing means to said display means during said predetermined scanning period, which is superimposed with said bloodflow-distribution image data.

17. The ultrasonic imaging system according to claim 11, wherein a plurality of ultrasonic scanned images are successively acquired from said ultrasonic image data producing means during said predetermined scanning period and said ultrasonic scanned image to be superimposed on said three-dimensional bloodflow-distribution image is the most recent of said successively acquired ultrasonic scanned images.

18. The ultrasonic imaging system according to claim 11, wherein said three-dimensional bloodflow-distribution image is displayed by said display means simultaneously with a two-dimensional color Doppler bloodflow-distribution image, said three-dimensional and two-dimensional bloodflow-distribution images being superimposed on the most recent ultrasonic image of a plurality of ultrasonic scanned images acquired from said ultrasonic image data producing means.

19. An ultrasonic imaging system comprising:

scanning means for scanning a biological body under medical examination within a three-dimensional volume by producing a plurality of successive two-dimensional scanning planes involving the biological body by utilizing ultrasonic pulses to obtain echo signals produced from echo pulses reflected from the biological body;

ultrasonic image data producing means for producing a plurality of ultrasonic scanned image data about the scanned biological body with regard to the successive scanning planes in response to said echo signals;

bloodflow-distribution image data producing means for producing a plurality of bloodflow-distribution image data about the scanned biological body with regard to the successive scanning planes in response to said echo signals;

storage means for temporarily storing said plurality of bloodflow-distribution image data, while sequentially updating and superimposing said plurality of bloodflow-distribution image data in such a manner that preceding bloodflow-distribution image data is updated/superimposed with present bloodflow-distribution image data; and display means for displaying a three-dimensional bloodflow-distribution image superimposed on an ultrasonic scanned image in a real time mode by processing both of latest bloodflow-distribution image data read out from said storage means and acquired during a predetermined scanning period and said ultrasonic scanned image data, wherein said display means includes a B-mode data DSC (digital scan converter) circuit having a plurality of frame memories for sequentially storing therein said plurality of ultrasonic scanned image data; and first and second multiplexers for selectively reading preselected ultrasonic scanned image data from said frame memories during said predetermined scanning period, which is superimposed with said bloodflow-distribution image data.

20. An ultrasonic imaging system comprising:

scanning means for scanning a biological body under medical examination within a three-dimensional volume by producing a plurality of successive two-dimensional scanning planes involving the biological body by utilizing ultrasonic pulses to obtain echo signals produced from echo pulses reflected from the biological body;

ultrasonic image data producing means for producing a plurality of ultrasonic scanned image data about the scanned biological body with regard to the successive scanning planes in response to said echo signals;

bloodflow-distribution image data producing means for producing a plurality of bloodflow-distribution image data about the scanned biological body with regard to the successive scanning planes in response to said echo signals;

storage means for temporarily storing said plurality of bloodflow-distribution image data, while sequentially updating and superimposing said plurality of bloodflow-distribution image data in such a manner that preceding bloodflow-distribution image data is updated/superimposed with present bloodflow-distribution image data; and display means for displaying a three-dimensional bloodflow-distribution image superimposed on an ultrasonic scanned image in a real time mode by processing both of latest bloodflow-distribution image data read out from said storage means and acquired during a predetermined scanning period and said ultrasonic scanned image data;

a third image memory unit arranged by a third image memory having a plurality of memory regions for sequentially storing therein said plurality of ultrasonic scanned image data derived from said ultrasonic image data producing means; and also by first and second multiplexers for selectively reading preselected ultrasonic scanned image data from said plurality of memory regions during said predetermined scanning period, which is superimposed with said bloodflow-distribution image data.

21. An ultrasonic imaging system comprising:

scanning means for scanning a biological body under medical examination within a three-dimensional volume by producing a plurality of successive two-dimensional scanning planes involving the biological body by utilizing ultrasonic pulses to obtain echo signals produced from echo pulses reflected from the biological body;

ultrasonic image data producing means for producing a plurality of ultrasonic scanned image data about the scanned biological body with regard to the successive scanning planes in response to said echo signals;

bloodflow-distribution image data producing means for producing a plurality of bloodflow-distribution image data about the scanned biological body with regard to the successive scanning planes in response to said echo signals;

storage means for temporarily storing said plurality of bloodflow-distribution image data, while sequentially updating and superimposing said plurality of bloodflow-distribution image data in such a manner that preceding bloodflow-distribution image data is updated/superimposed with present bloodflow-distribution image data;

display means for displaying a three-dimensional bloodflow-distribution image superimposed on an ultrasonic scanned image in a real time mode by processing both of latest bloodflow-distribution image data read out from said storage means and acquired during a predetermined scanning period and said ultrasonic scanned image data; and means for detecting scanning positions of said scanning means to produce positional data with respect to said scanning planes, whereby said storage means corrects superimposing positions of said plural bloodflow-distribution image data based upon said positional data.

22. An ultrasonic imaging system as claimed in claim 21, further comprising:

means interposed between said ultrasonic image data producing means and said display means, for selectively supplying preselected ultrasonic scanned image data from said producing means to said display means during said predetermined scanning period, which is superimposed with said bloodflow-distribution image data.

23. An ultrasonic imaging system as claimed in claim 21, wherein said display means includes a B-mode data DSC (digital scan converter) circuit having a plurality of frame memories for sequentially storing therein said plurality of ultrasonic scanned image data; and first and second multiplexers for selectively reading preselected ultrasonic scanned image data from said frame memories during said predetermined scanning period, which is superimposed with said bloodflow-distribution image data.

24. An ultrasonic imaging system as claimed in claim 21, wherein said display means includes a B-mode data DSC circuit arranged by a third image memory having a plurality of memory regions for sequentially storing therein said plurality of ultrasonic scanned image data; and also by first and second multiplexers for selectively reading preselected ultrasonic scanned image data from said plurality of memory regions during said predetermined scanning period, which is superimposed with said bloodflow-distribution image data.

25. An ultrasonic imaging system as claimed in claim 21, wherein a system controller is employed to control said display means for predetermining a scanning position of the ultrasonic scanned image data, whereby only said predetermined ultrasonic scanned image data is superimposed with said bloodflow-distribution image data.

* * * * *